(12) United States Patent
Jiang et al.

(10) Patent No.: US 6,908,619 B1
(45) Date of Patent: Jun. 21, 2005

(54) CAMP FACTOR OF *STREPTOCOCCUS UBERIS*

(75) Inventors: Min Jiang, Saskatchewan (CA); Andrew A. Potter, Saskatchewan (CA); Philip Ronald MacLachlan, Saskatchewan (CA)

(73) Assignee: University of Saskatchewan, Saskatchewan (CA)

(*) Notice: Subject to any disclaimer, the term of this patent is extended or adjusted under 35 U.S.C. 154(b) by 0 days.

(21) Appl. No.: 09/234,733

(22) Filed: Jan. 21, 1999

Related U.S. Application Data

(62) Division of application No. 08/658,277, filed on Jun. 5, 1996, now Pat. No. 5,863,543.
(60) Provisional application No. 60/000,083, filed on Jun. 8, 1995.

(51) Int. Cl.[7] .................. A61B 5/055; A01N 63/00; A61K 39/00; A61K 39/38; A61K 39/09

(52) U.S. Cl. ............... 424/244.1; 424/9.34; 424/93.44; 424/165.1; 424/184.1; 424/185.1; 424/190.1; 424/234.1; 424/237.1; 435/7.34; 435/68.1; 435/69.1; 435/69.3; 435/70.1; 435/71.1; 524/23.1; 530/388.4; 530/403; 536/23.4; 536/23.7; 930/290

(58) Field of Search .............................. 536/23.1, 23.4, 536/24.1, 23.7; 435/243, 253.4, 320.1, 69.7; 530/350, 820, 821, 825

(56) References Cited

FOREIGN PATENT DOCUMENTS

| EP | 0 626 452 A1 | 11/1994 |
|---|---|---|
| WO | WO 96/41879 A1 | 12/1996 |

OTHER PUBLICATIONS

Herzog et al. DNA and Cell Biology 12(6):465–471, 1993.*
Rudinger et al. "Peptide Hormones" Edit Ed by Parsons University Park Press, 1976.*
Burgess et al J Cell Biol 111:2129–2138, 1990.*
Levinson et al. Examination & Board Review Medical Microbiology & Immunology p. 292–293, 1974.*
Podbielski Med Microbiol Immunol 183:239–256, 1994.*
Williams Lett Appl Microbiol 12(1):23–8, 1991.*
Sambrook et al. Molecular Cloning, A Laboratory Manual C SH 1989, 17 Expression of Cloned Genes in *E coli*, 1989.*
George et al. Macromal Sequencing Synthesis Select Meth Appl Alan Liss Inc., 1988.*
Bernheimer et al., "Nature and Mechanism of Action of the CAMP Protein of Group B Streptococci," *Infection and Immunity* 23(3):838–844 (1979).
Christie et al., "A Note on a Lytic Phenomenon Shown by Group B Streptococci," *Aus. J. Exp. Bio. Med. Sci.* 22:197–200 (1944).
Fehrenbach et al., "Interaction of Amphiphilic Bacterial Polypeptides With Artifical Membranes," *Bacterial Protein Tokins*, pp. 317–324 (1984).
Rühlmann et al., "Complete Amino Acid Sequence of Protein B," *Fed. of Europ. Biochem. Soc.* 235(1,2):262–266 (1988).
Schneewind et al., "Cloning and Expression of the CAMP Factor of Group B Streptococci in *Escherichia coli*," *Infection & Immunity* 56(8):2174–2179 (1988).

(Continued)

*Primary Examiner*—Anthony Caputa
*Assistant Examiner*—J. Hines
(74) *Attorney, Agent, or Firm*—Robins & Pasternak LLP

(57) ABSTRACT

The CAMP factor gene of *Streptococcus uberis* (*S. uberis*) is described, as well as the recombinant production of CAMP factor therefrom. CAMP factors can be used in vaccine compositions for the prevention and treatment of bacterial infections.

24 Claims, 10 Drawing Sheets

OTHER PUBLICATIONS

Skalka et al., "Lethal Effect of CAMP–Factor and UBER-IS–Factor-a New Finding About Diffusible Exosubstances of *Streptococcus agalactiae* and *Streptococcus uberis*," *Zentralbl. Bakteriol. Ser. A 249*:190–194 (1981).

Sterzik et al., "Interaction of the Camp–Factor From *S.agalactiae* With Artificial Membranes," *Bacterial Protein Toxins*, pp. 195–196 (1984).

Sterzik et al., "Structure and Function of CAMP Factor of *Streptococcus agalactiae*," *Zentralbl. Bakteriol. Mikrobiol. Hyg. Abt. 1 15*:101–108 (1985).

Fehrenbach et al., "Role of CAMP–Factor (Protein B) for Virulence," (Eds.) *Bacterial Protein Toxins, Zbl. Bakt. Suppl. 17*:351–357 (1988).

Figura et al., "Differentiation of Motile and Mesophilic Aeromonas Strains Into Species by Testing for a CAMP–Like Factor," *J. Clin. Microbiol. 25*(7):1341–1342 (1987).

Fraser, Gordon, "Bacteriology: Haemolytic Activity of Corynebacterium," *Nature 189*:246 (1961).

Frey et al., "Cloning and Expression of a Cohemolysin, the CAMP Factor of *Actinobacillus pleuropneumoniae*," *Infection & Immunity 57*(7):2050–2056 (1989).

Jiang et al., Cloning, Sequencing and Expression of the CAMP Factor Gene of *Streptococcus uberis, 20*:297–307 (1996).

Jürgens et al., "Purification and Characterization of Camp–Factor From *Streptococcus agalactiae* by Hydrophobic Interaction Chromatography and Chromatofocusing," *Journal of Chromatography, 348*:363–370 (1985).

Jürgens et al., "Unspecific Binding of Group B *Streptococcal cocytolysin* (CAMP Factor) to Immunoglobulins and its Possible Roe in Pathogenicity," *J. Exp. Med. 165*:720–732 (1987).

Kohler, W., "CAMP–Like Phenomens of Vibrios," *Zentralbl. Bakteriol. Mikrobiol. Hyg. Ser. A 270*:35–40 (1988).

Rocourt et al., "Notes; *Listeria welshimeri* Sp. Nov. and *Listerie seeligeri* Sp. Nov.," *Internationl. J. Syst. Bacteriol, 33*(4):866–869 (1983).

Finch et al., "Further studies on the efficacy of a live vaccine against mastitis caused by *Streptococcus uberis*," Vaccine 15(10):1138–1143, 1997.

Fontaine et al., "Immunisation of dairy cattle with recombinant *treptococcus uberis* GapC or a chimeric CAMP antigen confers protection against heterologous bacterial challenge," Vaccine 20:2278–2286, 2002.

Fontaine et al., "Immunisation of dairy cattle with recombinant *Strptococcus uberis* GapC or a chimeric CAMP antigen confers protection against heterologous bacterial challenge," Vaccine 20:3047–3048, 2002.

Leigh et al., "Vaccination with the plasminogen activator from *Streptococcus uberis* induces an inhibitory response and protects against experimental infection in the dairy cow," Vaccine 17:851–857, 1997.

* cited by examiner

```
AATGAACATAAAATAAAAATTAATATATTTTATGATAATCACATATATTTGAC                        60
                                              ‾‾‾
                                              -35

TTAAAAAATTGTTACTGTATGATACAGGCATAAGTACTTATTTATTTTATAGATTGCAA                 120
                    ‾‾‾
                    -10
                                     +1

TTTATAAACAATTATATTTTTCAAAGAGGAATGCTT ATG GAA TTC AAA AAG TTA CTT TAT        180
                     ‾‾                Met Glu Phe Lys Lys Leu Leu Tyr>      8
                     SD                        SIGNAL PEPTIDE_a_____a____>

TTA ACT GGT TCA ATC GCA GGA ATT ACT TTA TTT TCC CCA ATT TTA ACA AGT GTC CAA GCA   240
Leu Thr Gly Ser Ile Ala Gly Ile Thr Leu Phe Ser Pro Ile Leu Thr Ser Val Gln Ala>   28
_a_____a_____a_____>

AAT CAA ATA AAT GTT AGT CAA CCA TCT AAT AAT GAA AGT AAT GTT ATT TCA CAG AAA AAA   300
Asn Gln Ile Asn Val Ser Gln Pro Ser Asn Asn Glu Ser Asn Val Ile Ser Gln Lys Lys>   48
_b_____b_____b__>

GAA GAA ATT GAT AAT AGT CTA AAT CAG GAA AGT GCT CAA CTA TAT GCC TTG AAA GAA GAT   360
Glu Glu Ile Asp Asn Ser Leu Asn Gln Glu Ser Ala Gln Leu Tyr Ala Leu Lys Glu Asp>   68
_b_____b_____b__>

GTT AAA GGA ACT GAG AAA CAA GAA CAA TCA GTT AAT TCA GCA ATT TCA GCT GTT GAA AAT TTA   420
Val Lys Gly Thr Glu Lys Gln Glu Gln Ser Val Asn Ser Ala Ile Ser Ala Val Glu Asn Leu>   88
_b_____b_____b__>
```

Fig. 4A

```
AAA ACT TCA CTT AGA GCT AAT CCT GAA ACA ATT TAT GAT TTA AAT TCG ATT GGA ACA AGA        480
Lys Thr Ser Leu Arg Ala Asn Pro Glu Thr Ile Tyr Asp Leu Asn Ser Ile Gly Thr Arg>      108
 b   b   b   b   b   b   b   b   b  MATURE PEPTIDE b   b   b   b   b   b   b   b

GTA GAA GCA ATC TCT GAC GTG ATT CAA GCA ATT GTT TTT TCA ACG CAA CAG TTA ACA AAT        540
Val Glu Ala Ile Ser Asp Val Ile Gln Ala Ile Val Phe Ser Thr Gln Gln Leu Thr Asn>      128
 b   b   b   b   b   b   b   b   b  MATURE PEPTIDE b   b   b   b   b   b   b   b

AAA GTT GAT CAA GCT CAC ATT GAT ATG GGA TTT GCT ATT ACG AAA TTA CTT ATT CGC ATT        600
Lys Val Asp Gln Ala His Ile Asp Met Gly Phe Ala Ile Thr Lys Leu Leu Ile Arg Ile>      148
 b   b   b   b   b   b   b   b   b  MATURE PEPTIDE b   b   b   b   b   b   b   b

GCA GAC CCA TTT GCT TCA AAT GAA TCC ATT AAA GGG CAA GTC GAA GCT GTT AAA CAA GTG        660
Ala Asp Pro Phe Ala Ser Asn Glu Ser Ile Lys Gly Gln Val Glu Ala Val Lys Gln Val>      168
 b   b   b   b   b   b   b   b   b  MATURE PEPTIDE b   b   b   b   b   b   b   b

CAA GCG ACT GTG CTT ACC TAT CCC GAT TTG CAG CCT ACG GAT AGA GCA ACT ATT TAC GTT        720
Gln Ala Thr Val Leu Thr Tyr Pro Asp Leu Gln Pro Thr Asp Arg Ala Thr Ile Tyr Val>      188
 b   b   b   b   b   b   b   b   b  MATURE PEPTIDE b   b   b   b   b   b   b   b

AAA TCA AAA TTA GAC AAG CTT ATT TGG CAA ACA AGA ATT ACC AGA GAT CAA AAA GTT CTT        780
Lys Ser Lys Leu Asp Lys Leu Ile Trp Gln Thr Arg Ile Thr Arg Asp Gln Lys Val Leu>      208
 b   b   b   b   b   b   b   b   b  MATURE PEPTIDE b   b   b   b   b   b   b   b

AAT GTA AAG AGT TTT GAA GTT TAT CAT CAA TTA AAT AAA GCT ATC ACA CAT GCA GTA GGT        840
Asn Val Lys Ser Phe Glu Val Tyr His Gln Leu Asn Lys Ala Ile Thr His Ala Val Gly>      228
 b   b   b   b   b   b   b   b   b  MATURE PEPTIDE b   b   b   b   b   b   b   b
```

Fig. 4B

```
GTA CAA TTA AAT CCA ACT GTA ACA GTT GCA CAA GTT GAC CAA GAA ATC AAA GTG CTA CAA    900
Val Gln Leu Asn Pro Thr Val Thr Val Ala Gln Val Asp Gln Glu Ile Lys Val Leu Gln>   248
    b   b   b   b   b   b   b   b   b   MATURE PEPTIDE b   b   b   b   b   b   b

GAA GCA TTA AAT ACT GCT CTA CAG TAAGGTAGAGATTGAATTGACGTATTAAAAAGGACT               960
Glu Ala Leu Asn Thr Ala Leu Gln >                                                  256
    b   MATURE PEPTIDE b   b   b

GGAATTTATTAATTTCAGTCCTTTAGAATTTTATTTAGCTGATTACTTGTTGAAGAGA                        1020

TTTGGTGGAAAATCAAGTACCATACTTCATTTCTCCCTCCAAATACTTGTATGTCGATTCC                     1080

CTTCTAAAACATAGCTAATTAGTTTAGTTTTCTGGCTAATAGATTGTACATGAAATTGTT                      1140

CAAAATTACTAGGGTAAAAGGTTTTCTTTTTATAAATTCATCATGACTAT                                1190
```

Fig. 4C

```
SUCAMP      - MEFKKLLYLTGSIAGITLFSPILTSVQANQINVSQP-----SNNESNVIS  -45
              :.    :            :::  .. ..
SAGCAMP     -                                   DQVTTPQVVNHVNSNNQAQQMA -22

SUCAMP      - QKKEEIDNSLNQESAQLYALKEDVKGTEKEQSVNSAISAVENLKTSLRAN  -95
              ::       :.: ::   .:.  : ::. :  :: ::..:: :::::::::
SAGCAMP     - QKL-------DQDSIQLRNIKDNVQGTDYEKPVNEAITSVEKLKTSLRAN  -65

SUCAMP      - PETIYDLNSIGTRVEAISDVIQAIVFSTQQLTNKVDQAHIDMGFAITKLL  -145
              ::.::::::::.::::..::: :: :::: :.::: :: :::::  ::::.
SAGCAMP     - SETVYDLNSIGSRVEALTDVIEAITFSTQHLANKVSQANIDMGFGITKLV  -115

SUCAMP      - IRIADPFASNESIKGQVEAVKQVQATVLTYPDLQPTDRATIYVKSKLDKL  -195
              :::  :::::  .::: ::   ::  .     ::::::: ::::::::: ::::::
SAGCAMP     - IRILDPFASVDSIKAQVNDVKALEQKVLTYPDLKPTDRATIYTKSKLDKE  -165

SUCAMP      - IWQTRITRDQKVLNVKSFEVYHQLNKAITHAVGVQLNPTVTVAQVDQEIK  -245
              ::.::  ::: ::::::  :  ::  :::::::::::::::  :::  :::::
SAGCAMP     - IWNTRFTRDKKVLNVKEFKVYNTLNKAITHAVGVQLNPNVTVQQVDQEIV  -215

SUCAMP      - VLQEALNTALQ  -256
              ::  :::.:::
SAGCAMP     - TLQAALQTALK  -226
```

Fig. 6

SEQUENCE LISTING

<160> NUMBER OF SEQ ID NOS: 5

<210> SEQ ID NO 1
<211> LENGTH: 1191
<212> TYPE: DNA
<213> ORGANISM: Artificial Sequence
<220> FEATURE:
<223> OTHER INFORMATION: Description of Artificial Sequence: S. uberis
      CAMP factor gene
<220> FEATURE:
<221> NAME/KEY: CDS
<222> LOCATION: (157)..(924)

<400> SEQUENCE: 1

```
aatgaacata aaataaaaat taataattat atatttttat gataatcaca tatatttgac      60
ttaaaaaaat tgttactgta tgatacaggc ataagtactt atttatttta tagattgcaa     120
tttataaaca attatatttt tcaaagagga atgctt atg gaa ttc aaa aag tta      174
                                        Met Glu Phe Lys Lys Leu
                                          1               5 ctt tat tta act ggt tca atc gca gga att act tta ttt tcc cca att     222
Leu Tyr Leu Thr Gly Ser Ile Ala Gly Ile Thr Leu Phe Ser Pro Ile
        10                  15                  20 tta aca agt gtc caa gca aat caa ata aat gtt agt caa cca tct aat     270
Leu Thr Ser Val Gln Ala Asn Gln Ile Asn Val Ser Gln Pro Ser Asn
    25                  30                  35 aat gaa agt aat gtt att tca cag aaa aaa gaa gaa att gat aat agt     318
Asn Glu Ser Asn Val Ile Ser Gln Lys Lys Glu Glu Ile Asp Asn Ser
40                  45                  50
```

-continued

```
cta aat cag gaa agt gct caa cta tat gcc ttg aaa gaa gat gtt aaa      366
Leu Asn Gln Glu Ser Ala Gln Leu Tyr Ala Leu Lys Glu Asp Val Lys
 55                  60                  65                  70 gga act gag aaa gaa caa tca gtt aat tca gca att tca gct gtt gaa      414
Gly Thr Glu Lys Glu Gln Ser Val Asn Ser Ala Ile Ser Ala Val Glu
             75                  80                  85 aat tta aaa act tca ctt aga gct aat cct gaa aca att tat gat tta      462
Asn Leu Lys Thr Ser Leu Arg Ala Asn Pro Glu Thr Ile Tyr Asp Leu
         90                  95                 100 aat tcg att gga aca aga gta gaa gca atc tct gac gtg att caa gca      510
Asn Ser Ile Gly Thr Arg Val Glu Ala Ile Ser Asp Val Ile Gln Ala
    105                 110                 115 att gtt ttt tca acg caa cag tta aca aat aaa gtt gat caa gct cac      558
Ile Val Phe Ser Thr Gln Gln Leu Thr Asn Lys Val Asp Gln Ala His
120                 125                 130 att gat atg gga ttt gct att acg aaa tta ctt att cgc att gca gac      606
Ile Asp Met Gly Phe Ala Ile Thr Lys Leu Leu Ile Arg Ile Ala Asp
135                 140                 145                 150 cca ttt gct tca aat gaa tcc att aaa ggg caa gtc gaa gct gtt aaa      654
Pro Phe Ala Ser Asn Glu Ser Ile Lys Gly Gln Val Glu Ala Val Lys
                155                 160                 165 caa gtg caa gcg act gtg ctt acc tat ccc gat ttg cag cct acg gat      702
Gln Val Gln Ala Thr Val Leu Thr Tyr Pro Asp Leu Gln Pro Thr Asp
            170                 175                 180 aga gca act att tac gtt aaa tca aaa tta gac aag ctt att tgg caa      750
Arg Ala Thr Ile Tyr Val Lys Ser Lys Leu Asp Lys Leu Ile Trp Gln
        185                 190                 195 aca aga att acc aga gat caa aaa gtt ctt aat gta aag agt ttt gaa      798
Thr Arg Ile Thr Arg Asp Gln Lys Val Leu Asn Val Lys Ser Phe Glu
    200                 205                 210 gtt tat cat caa tta aat aaa gct atc aca cat gca gta ggt gta caa      846
Val Tyr His Gln Leu Asn Lys Ala Ile Thr His Ala Val Gly Val Gln
215                 220                 225                 230 tta aat cca act gta aca gtt gca caa gtt gac caa gaa atc aaa gtg      894
Leu Asn Pro Thr Val Thr Val Ala Gln Val Asp Gln Glu Ile Lys Val
                235                 240                 245 cta caa gaa gca tta aat act gct cta cag taagtagag attgaattga         944
Leu Gln Glu Ala Leu Asn Thr Ala Leu Gln
            250                 255 cgtattaaaa aggactggaa tttattaatt tcagtccttt agaattttta tttagctgat   1004
ttacttgttg aagagatttg gtggaaaatc aagtaccata cttcatttct cctccaaata   1064
cttgtatgtc gattcccttc taaaacatag ctaattagtt tagttttctg gctaatagat   1124
tgtacatgaa attgttcaaa attactaggg taaaaggttt ttcttttttat aaattcatca   1184 tgactat                                                             1191
```

<210> SEQ ID NO 2
<211> LENGTH: 256
<212> TYPE: PRT
<213> ORGANISM: Artificial Sequence
<220> FEATURE:
<223> OTHER INFORMATION: Description of Artificial Sequence: CAMP factor
      preprotein

<400> SEQUENCE: 2

Met Glu Phe Lys Lys Leu Leu Tyr Leu Thr Gly Ser Ile Ala Gly Ile
 1               5                  10                  15

Thr Leu Phe Ser Pro Ile Leu Thr Ser Val Gln Ala Asn Gln Ile Asn
            20                  25                  30

```
Val Ser Gln Pro Ser Asn Asn Glu Ser Asn Val Ile Ser Gln Lys Lys
            35                  40                  45

Glu Glu Ile Asp Asn Ser Leu Asn Gln Glu Ser Ala Gln Leu Tyr Ala
        50                  55                  60

Leu Lys Glu Asp Val Lys Gly Thr Glu Lys Gln Ser Val Asn Ser
 65                  70                  75                  80

Ala Ile Ser Ala Val Glu Asn Leu Lys Thr Ser Leu Arg Ala Asn Pro
                85                  90                  95

Glu Thr Ile Tyr Asp Leu Asn Ser Ile Gly Thr Arg Val Glu Ala Ile
            100                 105                 110

Ser Asp Val Ile Gln Ala Ile Val Phe Ser Thr Gln Leu Thr Asn
            115                 120                 125

Lys Val Asp Gln Ala His Ile Asp Met Gly Phe Ala Ile Thr Lys Leu
 130                 135                 140

Leu Ile Arg Ile Ala Asp Pro Phe Ala Ser Asn Glu Ser Ile Lys Gly
 145                 150                 155                 160

Gln Val Glu Ala Val Lys Gln Val Gln Ala Thr Val Leu Thr Tyr Pro
            165                 170                 175

Asp Leu Gln Pro Thr Asp Arg Ala Thr Ile Tyr Val Lys Ser Lys Leu
            180                 185                 190

Asp Lys Leu Ile Trp Gln Thr Arg Ile Thr Arg Asp Gln Lys Val Leu
        195                 200                 205

Asn Val Lys Ser Phe Glu Val Tyr His Gln Leu Asn Lys Ala Ile Thr
        210                 215                 220

His Ala Val Gly Val Gln Leu Asn Pro Thr Val Thr Val Ala Gln Val
 225                 230                 235                 240

Asp Gln Glu Ile Lys Val Leu Gln Glu Ala Leu Asn Thr Ala Leu Gln
            245                 250                 255

<210> SEQ ID NO 3
<211> LENGTH: 256
<212> TYPE: PRT
<213> ORGANISM: Artificial Sequence
<220> FEATURE:
<223> OTHER INFORMATION: Description of Artificial Sequence: deduced S.
      uberis CAMP factor protein

<400> SEQUENCE: 3

Met Glu Phe Lys Lys Leu Leu Tyr Leu Thr Gly Ser Ile Ala Gly Ile
 1               5                  10                  15

Thr Leu Phe Ser Pro Ile Leu Ser Val Gln Ala Asn Gln Ile Asn
            20                  25                  30

Val Ser Gln Pro Ser Asn Asn Glu Ser Asn Val Ile Ser Gln Lys Lys
            35                  40                  45

Glu Glu Ile Asp Asn Ser Leu Asn Gln Glu Ser Ala Gln Leu Tyr Ala
        50                  55                  60

Leu Lys Glu Asp Val Lys Gly Thr Glu Lys Gln Ser Val Asn Ser
 65                  70                  75                  80

Ala Ile Ser Ala Val Glu Asn Leu Lys Thr Ser Leu Arg Ala Asn Pro
                85                  90                  95

Glu Thr Ile Tyr Asp Leu Asn Ser Ile Gly Thr Arg Val Glu Ala Ile
            100                 105                 110

Ser Asp Val Ile Gln Ala Ile Val Phe Ser Thr Gln Leu Thr Asn
            115                 120                 125

Lys Val Asp Gln Ala His Ile Asp Met Gly Phe Ala Ile Thr Lys Leu
 130                 135                 140
```

```
Leu Ile Arg Ile Ala Asp Pro Phe Ala Ser Asn Glu Ser Ile Lys Gly
145                 150                 155                 160

Gln Val Glu Ala Val Lys Gln Val Gln Ala Thr Val Leu Thr Tyr Pro
                165                 170                 175

Asp Leu Gln Pro Thr Asp Arg Ala Thr Ile Tyr Val Lys Ser Lys Leu
            180                 185                 190

Asp Lys Leu Ile Trp Gln Thr Arg Ile Thr Arg Asp Gln Lys Val Leu
        195                 200                 205

Asn Val Lys Ser Phe Glu Val Tyr His Gln Leu Asn Lys Ala Ile Thr
    210                 215                 220

His Ala Val Gly Val Gln Leu Asn Pro Thr Val Thr Val Ala Gln Val
225                 230                 235                 240

Asp Gln Glu Ile Lys Val Leu Gln Glu Ala Leu Asn Thr Ala Leu Gln
                245                 250                 255

<210> SEQ ID NO 4
<211> LENGTH: 226
<212> TYPE: PRT
<213> ORGANISM: Artificial Sequence
<220> FEATURE:
<223> OTHER INFORMATION: Description of Artificial Sequence: S.
      agalactiae CAMP factor protein

<400> SEQUENCE: 4

Asp Gln Val Thr Thr Pro Gln Val Val Asn His Val Asn Ser Asn Asn
1               5                   10                  15

Gln Ala Gln Gln Met Ala Gln Lys Leu Asp Gln Asp Ser Ile Gln Leu
            20                  25                  30

Arg Asn Ile Lys Asp Asn Val Gln Gly Thr Asp Tyr Glu Lys Pro Val
        35                  40                  45

Asn Glu Ala Ile Thr Ser Val Glu Lys Leu Lys Thr Ser Leu Arg Ala
    50                  55                  60

Asn Ser Glu Thr Val Tyr Asp Leu Asn Ser Ile Gly Ser Arg Val Glu
65                  70                  75                  80

Ala Leu Thr Asp Val Ile Glu Ala Ile Thr Phe Ser Thr Gln His Leu
                85                  90                  95

Ala Asn Lys Val Ser Gln Ala Asn Ile Asp Met Gly Phe Gly Ile Thr
            100                 105                 110

Lys Leu Val Ile Arg Ile Leu Asp Pro Phe Ala Ser Val Asp Ser Ile
        115                 120                 125

Lys Ala Gln Val Asn Asp Val Lys Ala Leu Glu Gln Lys Val Leu Thr
    130                 135                 140

Tyr Pro Asp Leu Lys Pro Thr Asp Arg Ala Thr Ile Tyr Thr Lys Ser
145                 150                 155                 160

Lys Leu Asp Lys Glu Ile Trp Asn Thr Arg Phe Thr Arg Asp Lys Lys
                165                 170                 175

Val Leu Asn Val Lys Glu Phe Lys Val Tyr Asn Thr Leu Asn Lys Ala
            180                 185                 190

Ile Thr His Ala Val Gly Val Gln Leu Asn Pro Asn Val Thr Val Gln
        195                 200                 205

Gln Val Asp Gln Glu Ile Val Thr Leu Gln Ala Ala Leu Gln Thr Ala
    210                 215                 220

Leu Lys
225
```

-continued

```
<210> SEQ ID NO 5
<211> LENGTH: 228
<212> TYPE: PRT
<213> ORGANISM: Artificial Sequence
<220> FEATURE:
<223> OTHER INFORMATION: Description of Artificial Sequence: mature S.
      uberis CAMP factor protein

<400> SEQUENCE: 5

Asn Gln Ile Asn Val Ser Gln Pro Ser Asn Asn Glu Ser Asn Val Ile
 1               5                  10                  15

Ser Gln Lys Lys Glu Glu Ile Asp Asn Ser Leu Asn Gln Glu Ser Ala
            20                  25                  30

Gln Leu Tyr Ala Leu Lys Glu Asp Val Lys Gly Thr Glu Lys Glu Gln
        35                  40                  45

Ser Val Asn Ser Ala Ile Ser Ala Val Glu Asn Leu Lys Thr Ser Leu
    50                  55                  60

Arg Ala Asn Pro Glu Thr Ile Tyr Asp Leu Asn Ser Ile Gly Thr Arg
65                  70                  75                  80

Val Glu Ala Ile Ser Asp Val Ile Gln Ala Ile Val Phe Ser Thr Gln
                85                  90                  95

Gln Leu Thr Asn Lys Val Asp Gln Ala His Ile Asp Met Gly Phe Ala
            100                 105                 110

Ile Thr Lys Leu Leu Ile Arg Ile Ala Asp Pro Phe Ala Ser Asn Glu
        115                 120                 125

Ser Ile Lys Gly Gln Val Glu Ala Val Lys Gln Val Gln Ala Thr Val
    130                 135                 140

Leu Thr Tyr Pro Asp Leu Gln Pro Thr Asp Arg Ala Thr Ile Tyr Val
145                 150                 155                 160

Lys Ser Lys Leu Asp Lys Leu Ile Trp Gln Thr Arg Ile Thr Arg Asp
                165                 170                 175

Gln Lys Val Leu Asn Val Lys Ser Phe Glu Val Tyr His Gln Leu Asn
            180                 185                 190

Lys Ala Ile Thr His Ala Val Gly Val Gln Leu Asn Pro Thr Val Thr
        195                 200                 205

Val Ala Gln Val Asp Gln Glu Ile Lys Val Leu Gln Glu Ala Leu Asn
    210                 215                 220

Thr Ala Leu Gln
225
```

CAMP FACTOR OF *STREPTOCOCCUS UBERIS*

This application is a divisional of U.S. patent application Ser. No. 08/658,277 filed on Jun. 5, 1996, now U.S. Pat. No. 5,863,543, which claims priority to U.S. provisional patent application Ser. No. 60/000,083 filed on Jun. 8, 1995.

TECHNICAL FIELD

The present invention relates generally to bacterial antigens. More particularly, the present invention pertains to the recombinant production of CAMP factor from *Streptococcus uberis* (*S. uberis*) and the use of CAMP factors in vaccine compositions.

BACKGROUND

*S. uberis* is an important cause of mastitis in dairy cattle and is responsible for about 20% of all clinical cases of mastitis (Bramley, A. J. and Dodd, F. H. (1984) *J. Dairy Res.* 51:481–512; Bramley, A. J. (1987) *Animal Health Nutrition* 42:12–16; Watts, J. L. (1988) *J. Dairy Sci.* 71:1616–1624). Since antimicrobial treatment is generally ineffective in treating *S. uberis* mastitis, the development of control measures must be based on an understanding of virulence factors and protective antigens involved in invasion and protection of the mammary gland (Collins et al. (1988) *J. Dairy Res.* 55:25–32; Leigh et al. (1990) *Res. Vet. Sci.* 49: 85–87; Marshall et al. (1986) *J. Dairy Res.* 53: 507–514).

It is known that some *S. uberis* strains can produce hyaluronic acid capsule (Hill, A. W. (1988) *Res. Vet. Sci.* 45:400–404), hyaluronidase (Schaufuss et al. (1989) *Zentralbl. Bakteriol. Ser. A* 271:46–53), R-like protein (Groschup, M. H. and Timoney, J. F. (1993) *Res. Vet. Sci.* 5:124–126), and a cohemolysin, the CAMP factor, also known as UBERIS factor (Skalka, B. and Smola, J. (1981) *Zentralbl. Bakteriol. Ser. A* 249:190–194). However, very little is known of their roles in pathogenicity.

The effect of CAMP factor was first described by Christie et al. in 1944 (Christie et al. (1944) *Aus. J. Exp. Biol. Med. Sci.* 22:197–200). These authors found that group B streptococci (GBS), such as *S. agalactiae*, produced a distinct zone of complete hemolysis when grown near the diffusion zone of the *Staphylococcus aureus* beta-toxin, sphingomyelinase. This phenomenon was called CAMP reaction and the compound for this reaction was characterized as the CAMP factor, an extracellular protein with a molecular weight of 23,500 (Bernheimer et al. (1979) *Infect. Immun.* 23:838–844). The CAMP factor was subsequently purified from *S. agalactiae* and characterized as a 25,000 Da protein with a pI of 8.9 (Jürgens at al. (1985) *J. Chrom.* 3:363–370). The amino acid sequence of *S. agalactiae* CAMP factor was determined by Rühlmann et al. (Rühlmann et al. (1988) *FEBS Lett* 235:262–266).

The mechanism of the CAMP reaction has been described. See, e.g., Bernheimer et al. (1979) *Infect. Immun.* 23:838–844; Sterzik et al. "Interaction of the CAMP factor from *S. agalactiae* with artificial membranes." In: Alouf et al., eds. *Bacterial protein toxins*, London: Academic Press Inc, 1984; 195–196; Sterzik et al. (1985) *Zentralbl. Bakteriol. Mikrobiol. Hyg. Abt.* 1 *Suppl.* 15:101–108; Fehrenbach et al. "Role of CAMP-factor (protein B) for virulence." In: Fehrenbach et al., eds. *Bacterial protein toxins*, Stuttgart: Gustav Fischer Verlag, 1988; 351–357; Fehrenbach et al. "Interaction of amphiphilic bacterial polypeptides with artificial membranes." In: Alouf et al., eds. *Bacterial protein toxins*, London: Academic Press Inc., 1984:317–324.

CAMP factor has lytic action on a variety of target cells including sheep and bovine erythrocytes, as well as on artificial membranes in which membrane phospholipids and sphingomyelin have been hydrolyzed by phospholipase or sphingomyelinase.

The role of CAMP factor in pathogenicity is unclear. A partially purified CAMP factor from *S. agalactiae* has been shown to be lethal to rabbits when injected intravenously (Skalka, B. and Smola, J. (1981) *Zentralbl. Bakteriol. Ser. A* 249:190–194). Furthermore, intraperitoneal injection of purified CAMP factor into mice has been shown to significantly raise the pathogenicity of a sublethal dose of group B streptococci (Fehrenbach et al. "Role of CAMP-factor (protein B) for virulence." In: Fehrenbach et al., eds. *Bacterial protein toxins*, Stuttgart: Gustav Fischer Verlag, 1988; 351–357). Additionally, like protein A of *S. aureus*, GBS CAMP factor can bind the Fc sites of immunoglobulins and has therefore been designated protein B (Jürgens et al. (1987) *J. Exp. Med.* 165:720–732).

In addition to GBS and *S. uberis*, other bacteria, including *Listeria monocytogenes* and *Listeria seeligeri* (Rocourt, J. and Grimont, P. A. D. (1983) *Int. J. Syst. Bacteriol.* 33:866–869) Aeromonas sp. (Figura, N. and Guglielmetti, P. (1987) *J. Clin. Microbiol.* 25:1341–1342), *Rhodococcus equi* (Fraser, G. (1961) *Nature* 189:246), and certain Vibrio spp. (Kohler, W. (1988) *Zentralbl. Bakteriol. Mikrobiol. Hyg. Ser. A* 270:35–40) produce reactions similar to the CAMP effect.

The CAMP factor genes of GBS and *A. pleuropneumoniae* have been cloned and expressed in *Escherichia coli* (Frey et al. (1989) *Infect. Immun.* 57:2050–2056; Schneewind et al. (1988) *Infect. Immun.* 56:2174–2179).

However, until now, the CAMP factor gene of *S. uberis* has not been cloned. Furthermore, the protective capability of CAMP factor has not been previously studied.

DISCLOSURE OF THE INVENTION

The present invention is based on the discovery of the CAMP factor gene of *S. uberis*, as well as the discovery that the CAMP factor is able to protect vertebrate subjects from infection. The CAMP factor, active immunogenic fragments thereof, active analogs thereof, or chimeric proteins including the same, can be used, either alone or in combination with other antigens, in novel subunit vaccines to provide protection from bacterial infection in vertebrate subjects.

Accordingly, in one embodiment, the subject invention is directed to an isolated nucleic acid molecule comprising a coding sequence for an immunogenic *Streptococcus uberis* CAMP factor. In additional embodiments, the invention is directed to recombinant vectors including the same, host cells transformed with these vectors and methods of recombinantly producing *S. uberis* CAMP factor.

In still further embodiments, the subject invention is directed to vaccine compositions comprising a pharmaceutically acceptable vehicle and an immunogenic CAMP factor. In particularly preferred embodiments, the CAMP factor is a Streptococcus CAMP factor.

In yet other embodiments, the present invention is directed to methods of treating or preventing bacterial infection, including streptococcal infections and mastitis, in a subject comprising administering to the subject a therapeutically effective amount of the above vaccine compositions.

In additional embodiments, the invention pertains to methods of producing vaccine compositions comprising (a) providing at least one immunogenic CAMP factor; and (b) combining the CAMP factor with a pharmaceutically acceptable vehicle.

These and other embodiments of the present invention will readily occur to those of ordinary skill in the art in view of the disclosure herein.

BRIEF DESCRIPTION OF THE FIGURES

FIG. 3A shows a coomassie blue-stained 12% polyacrylamide-SDS gel. Lane 1, partially purified *S. uberis* CAMP factor; lane 2, supernatant of *E. coli* JF1754(pJLD21)(CAMP positive); lane 3, supernatant of *E. coli* JF1754(pTZ18R)(CAMP negative); lane 4, supernatant of *S. agalactiae*; lane MW, prestained molecular weight standards. Numbers on the left of the figure indicate the positions of the molecular weight markers (in thousands). FIG. 3B shows an immunoblot of the gel presented in FIG. 3A. Samples were transferred to a nitrocellulose membrane and reacted with mouse antiserum against purified *S. uberis* CAMP factor.

FIGS. 4A–4C (SEQ ID NOS:1—2) show the nucleotide sequence of *S. uberis* CAMP factor gene and its promoter region. The start site of transcription is represented by +1, and the −10 and −35 regions of the promoter are indicated by the underlines. The putative Shine-Dalgarno sequence is shown as SD. The deduced amino acid sequence of *S. uberis* CAMP factor is shown using the three-letter code below the nucleotide sequence. The signal peptide and mature peptide are specified.

FIG. 6 (SEQ ID NOS:3—4) shows a comparison between *S. uberis* CAMP factor (upper lines, designated as "SUCAMP") and *S. agalactiae* CAMP factor (low lines, designated as "SAGCAMP"). Amino acids are identified in the single-letter code. Identical amino acids are indicated by double dots (:). The aligned sequences show 66.4% identity. Spaces (indicated by dash) were introduced in the sequences to optimize alignment.

DETAILED DESCRIPTION

Figure 1:
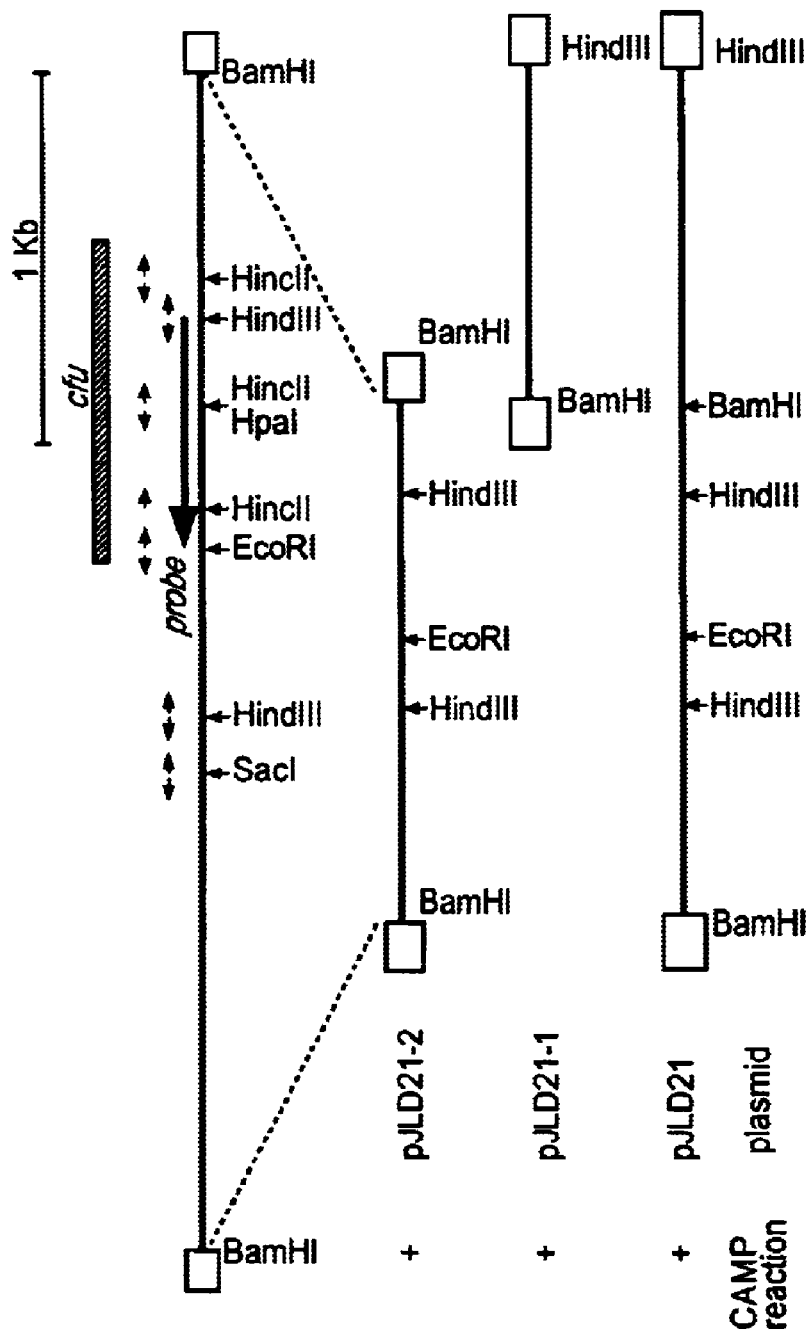
FIG. 1 depicts restriction enzyme maps of recombinant plasmid pJLD21 and subclones thereof, designated pJLD21-1 and pJLD21-2. Lines indicate *S. uberis* insert DNA, while boxes represent the multiple cloning sites of vector pTZ18R. The CAMP activities of recombinant plasmid pJLD21 and its derived subclones are indicated on the right (+, CAMP reaction positive; −, CAMP reaction negative). The small horizontal arrows represent start points and directions of sequencing experiments. The probe fragment used for Southern blot experiments is indicated by the large arrow. The bar at the bottom indicates the location of the open reading frame of CAMP factor gene of *S. uberis* (cfu).

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All publications, patents and patent applications cited herein, whether supra or infra, are hereby incorporated by reference in their entirety.

A. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a CAMP factor" includes a mixture of two or more CAMP factors, and the like.

The term "CAMP factor" or a nucleotide sequence encoding the same, intends a protein or a nucleotide sequence, respectively, which is derived from a CAMP factor gene found in a variety of bacterial species, including, without limitation *Streptococcus uberis*, group B streptococci (GBS) such as *S. agalactiae* (Jürgens et al. (1985) *J. Chromatogr.* 348:363–370; and Rühlmann et al. (1988) *FEBS Lett* 235:262–266), *Listeria monocytogenes* and *Listeria seeligeri* (Rocourt, J. and Grimont, P. A. D. (1983) *Int. J. Syst. Bacteriol.* 33:866–869), Aeromonas sp. (Figura, N. and Guglielmetti, P. (1987) *J. Clin. Microbiol.* 25:1341–1342), *Rhodococcus equi* (Fraser, G. (1961) *Nature* 189:246), and certain Vibrio spp. (Kohler, W. (1988) *Zentralbl. Bakteriol. Mikrobiol. Hyg. Ser. A* 270:35–40).

A representative CAMP factor gene, derived from *S. uberis*, is found in plasmid pJLD21 (ATCC Accession No. 69837) and depicted in FIGS. 4A–4C (SEQ ID NOS:1—2).

The derived protein or nucleotide sequences need not be physically derived from the gene described above, but may be generated in any manner, including for example, chemical synthesis, isolation (e.g., from an organism that produces the CAMP factor) or by recombinant production, based on the information provided herein.

Furthermore, the term intends proteins having amino acid sequences substantially homologous to contiguous amino acid sequences encoded by the genes, which display immunological activity. Thus, the terms include full-length, as well as immunogenic and truncated and partial sequences, as well as active analogs and precursor forms of the proteins, such as those forms including the signal sequence, described more fully below.

The terms also include proteins in neutral form or in the form of basic or acid addition salts depending on the mode of preparation. Such acid addition salts may involve free amino groups and basic salts may be formed with free carboxyls. Pharmaceutically acceptable basic and acid addition salts are discussed further below. In addition, the proteins may be modified by combination with other biological materials such as lipids (both those occurring naturally with the molecule or other lipids that do not destroy immunological activity) and saccharides, or by side chain modification, such as acetylation of amino groups, phosphorylation of hydroxyl side chains, oxidation of sulfhydryl groups, glycosylation of amino acid residues, as well as other modifications of the encoded primary sequence.

The term therefore intends deletions, additions and substitutions to the sequence, so long as the polypeptide functions to produce an immunological response as defined above. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule, but possessing minor amino acid substitutions that do not substantially affect the immunogenicity of the protein, are therefore within the definition of the reference polypeptide.

The term "streptococcal CAMP factor" intends a CAMP factor, as defined above, derived from a streptococcal species that produces the same, including *S. uberis* and GBS such as *S. agalactiae*. An "*S. uberis* CAMP factor" is a CAMP factor as defined above, derived from *S. uberis*.

By "mastitis" is meant an inflammation of the mammary gland in mammals, including in cows, ewes, goats, sows, mares, and the like, caused by various bacteria that produce CAMP factors, described more fully below. The infection manifests itself by the infiltration of phagocytic cells in the gland. Generally, 4 clinical types of mastitis are recognized: (1) peracute, associated with swelling, heat, pain, and abnormal secretion in the gland and accompanied by fever and other signs of systemic disturbance, such as marked depression, rapid weak pulse, sunken eyes, weakness and complete anorexia; (2) acute, with changes in the gland similar to those above but where fever, anorexia and depression are slight to moderate; (3) subacute, where no systemic changes are displayed and the changes in the gland and its secretion are less marked: and (4) subclinical, where the inflammatory reaction is detectable only by standard tests for mastitis.

Standard tests for the detection of mastitis include but are not limited to, the California Mastitis Test, the Wisconsin Mastitis Test, the Nagase test, the electronic cell count and somatic cell counts used to detect a persistently high white blood cell content in milk. In general, a somatic cell count of about 300,000 to about 500,000 cells per ml or higher, in milk will indicate the presence of infection. Thus, a vaccine is considered effective in the treatment and/or prevention of mastitis when, for example, the somatic cell count in milk is retained below about 500,000 cells per ml. For a discussion of mastitis and the diagnosis thereof, see, e.g., *The Merck Veterinary Manual. A Handbook of Diagnosis, Therapy, and Disease Prevention and Control for the Veterinarian*, Merck and Co., Rahway, N.J., 1991.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "epitope" refers to the site on an antigen or hapten to which specific B cells and T cells respond. The term is also used interchangeably with if "antigenic determinant" or "antigenic determinant site." Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display a protective immunological response to the CAMP factor in question, e.g., the host will be protected from subsequent infection by the pathogen and such protection will be demonstrated by either a reduction or lack of symptoms normally displayed by an infected host or a quicker recovery time.

The terms "immunogenic" protein or polypeptide refer to an amino acid sequence which elicits an immunological response as described above. An "immunogenic" protein or polypeptide, as used herein, includes the full-length sequence of the CAMP factor in question, including the precursor and mature forms, analogs thereof, or immunogenic fragments thereof. By "immunogenic fragment" is meant a fragment of a CAMP factor which includes one or more epitopes and thus elicits the immunological response described above. Such fragments can be identified by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Aced. Sci. USA* 81:3998–4002; Geysen et al. (1986) *Molec. Immu-*

*nol.* 23:709–715, all incorporated herein by reference in their entireties.

Immunogenic fragments, for purposes of the present invention, will usually be at least about 2 amino acids in length, more preferably about 5 amino acids in length, and most preferably at least about 10 to 15 amino acids in length. There is no critical upper limit to the length of the fragment, which could comprise nearly the full-length of the protein sequence, or even a fusion protein comprising two or more epitopes of the CAMP factor or factors in question.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "vector" is a replicon, such as a plasmid, phage, or cosmid, to which another DNA segment may be attached so as to bring about the replication of the attached segment.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

Similarly, a coding sequence is "operably linked to" another coding sequence (i.e., in the case of a chimeric protein) when RNA polymerase will transcribe the two coding sequences into mRNA, which is then translated into the polypeptides encoded by the two coding sequences. The coding sequences need not be contiguous to one another so long as the transcribed sequence is ultimately processed to produce the desired protein.

A control element, such as a promoter, "directs the transcription" of a coding sequence in a cell when RNA polymerase will bind the promoter and transcribe the coding sequence into mRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs such as ALIGN, Dayhoff, M. O. (1978) in *Atlas of Protein Sequence and Structure* 5:Suppl. 3, National biomedical Research Foundation, Washington, D.C.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra.

The term "functionally equivalent" intends that the amino acid sequence of the CAMP factor is one that will elicit a substantially equivalent or enhanced immunological response, as defined above, as compared to the response elicited by a CAMP factor having identity with either the mature sequence for the reference CAMP factor, or an immunogenic portion thereof.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

The term "treatment" as used herein refers to either (i) the prevention of infection or reinfection (prophylaxis), or (ii) the reduction or elimination of symptoms of the disease of interest (therapy).

By "vertebrate subject" is meant any member of the subphylum chordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds; and fish. The term does not denote a particular age. Thus, both adult and newborn animals, as well as fetuses, are intended to be covered.

B. General Methods

Central to the present invention is the discovery that the CAMP factor is capable of eliciting a protective immune response in a vertebrate subject. The gene for the *S. uberis* CAMP factor has been isolated and characterized and the CAMP factor encoded thereby sequenced. The protein product from the *S. uberis* CAMP factor gene has been shown to protect cattle from subsequent challenge with *S. uberis*.

In particular, the complete DNA sequence of *S. uberis* CAMP factor is shown in FIGS. 4A–4C (SEQ ID No:3—4). A major transcript of the CAMP factor gene is found beginning with an "A" residue (depicted at the +1 position in FIG. 4A). −10 and −35 regions, characteristic of *E. coli* promoters (Harley, C. B. and Reynolds, R. P. (1987) *Nucleic Acids Res*. 15:2343–2361), are found upstream of the transcriptional start site, as indicated in FIG. 4A. An open reading frame beginning with an ATG codon is located at positions 157 to 159 and terminates with a TAA stop codon at positions 925 to 927. The ATG start codon is preceded by the purine-rich sequence AAGAGG, which serves as a ribosome binding site in *E. coli* (Stormo et al. (1982) *Nucleic Acids Res*. 10:2971–2996).

As shown in FIGS. 4A–4C, the *S. uberis* CAMP factor gene encodes a preprotein of about 256 amino acids (amino acid residues 1 through 256, inclusive, of FIGS. 4A–4C) that includes an N-terminal signal sequence approximately 28 amino acids in length. The precursor molecule has a calculated molecular weight of 28,363 Da. The mature *S. uberis* CAMP factor thus includes amino acid residues 29 through 256 (SEQ ID NO:5), inclusive, as depicted in FIGS. 4A–4C. As discussed further below, the portion of the CAMP factor gene encoding the signal sequence can be included in constructs that encode the CAMP factor signal sequence and the CAMP factor upon expression. Additionally, the CAMP factor signal sequence and the nucleic acid sequence encoding the same can be used with heterologous proteins and nucleic acid molecules, to aid in the secretion thereof.

As shown in FIG. 6 (SEQ ID NOS:1—2), alignment of the 226-amino acid sequence of the *S. agalactiae* CAMP factor with the deduced 256 amino acids of the *S. uberis* CAMP factor shows that 66.4% of the amino acid residues are identical. Additionally, antibodies raised against purified *S. uberis* CAMP factor cross-react with *S. agalactiae* protein B. As shown in the examples, the *S. uberis* CAMP factor is secreted when produced recombinantly in *E. coli*.

The exact localization and sequence of the CAMP factor gene allows for in vitro mutagenesis studies to assess the functions of different domains on the CAMP protein. Also, the present data permits the generation of stable CAMP factor-synthesis deficient mutants through gene replacement and other molecular techniques. Comparison of the virulence of native and mutant *S. uberis* strains in animals provides important information regarding the contribution of the CAMP factor to the pathogenicity of bacteria expressing CAMP factors.

The CAMP factors, immunogenic fragments thereof or chimeric proteins including the same, can be provided in subunit vaccine compositions. In addition to use in vaccine compositions, the proteins or antibodies thereto can be used as diagnostic reagents to detect the presence of infection in a vertebrate subject. Similarly, the genes encoding the proteins can be cloned and used to design probes to detect and isolate homologous genes in other bacterial strains.

The vaccine compositions of the present invention can be used to treat or prevent a wide variety of bacterial infections in vertebrate subjects. For example, vaccine compositions including CAMP factors from *S. uberis* and/or group B streptococci (GBS), such as *S. agalactiae*, can be used to treat streptococcal infections in vertebrate subjects that are caused by these species. In particular, *S. uberis* and *S. agalactiae* are common bacterial pathogens associated with mastitis in bovine, equine, ovine and goat species. Additionally, group B streptococci, such as *S. agalactiae*, are known to cause numerous other infections in vertebrates, including septicemia, meningitis, bacteremia, impetigo, arthritis, urinary tract infections, abscesses, spontaneous abortion etc. Hence, vaccine compositions containing streptococcal CAMP factors will find use in treating and/or preventing a wide variety of streptococcal infections.

Similarly, CAMP factors derived from *Listeria monocytogenes* and *L. seeligeri*, Aeromonas sp., *Rhodococcus equi*, and Vibrio spp. will find use for treating bacterial infections caused by these species. For example, CAMP factors can be used to prevent or treat listeriosis in a wide range of animals and birds, including humans. The infection can manifest itself as encephalitis and meningoencephalitis in ruminants and avian species such as geese, chickens, turkeys, ducks, canaries and parrots; septicemia in monogastric animals, neonatal ruminants and poultry; and spontaneous abortion and latent infections in a wide variety of animals. Aeromonas causes infections in fish, including in salmonids, aquarium fish, goldfish, freshwater and marine fish; as well as infections in caged birds and in amphibians and reptiles. *Rhodococcus equi* causes respiratory infections, lymphangitis, peritonitis, enteritis, abscesses and spontaneous abortion in horses. Vibrio causes vibriosis in many cultured, aquarium and wild marine and estuarine fish; infections of open wounds in cetaceans; and avian vibrionic hepatitis and avian infectious hepatitis in chickens.

Thus, it is readily apparent that CAMP factor vaccines can be used to treat and/or prevent a wide variety of bacterial infections in numerous species.

CAMP factors from various species can be used either alone or in combination in the vaccine compositions of the present invention. For example, it will sometimes be preferable to have more than one epitope of one or more of the CAMP factors in the vaccine compositions of the present invention so that the subject in question can be provided with a broad spectrum of protection against infection. In its simplest form, this can be achieved by employing a polypeptide encoding the complete sequence of one of the CAMP factors, or by employing a combination of polypeptides encoding the sequences of two or more of the CAMP factors or epitopes of the CAMP factors. Thus, the vaccine compositions could comprise, for example various combinations of one or more of the CAMP factors, or a combination of several of the CAMP factors, or even several epitopes derived from the CAMP factors.

Furthermore, the vaccine compositions of the present invention can include other bacterial, fungal, viral or protozoal antigens. These antigens can be provided separately of even as fusion proteins comprising fragments of one or more of the CAMP factors fused to these antigens.

Production of the CAMP Factors

The above described CAMP factors and active fragments, analogs and chimeric proteins derived from the same, can be produced by a variety of methods. Specifically, the CAMP factors can be isolated directly from bacteria which express the same. This is generally accomplished by first preparing a crude extract which lacks cellular components and several extraneous proteins. The desired proteins can then be further purified i.e. by column chromatography, HPLC, immunoadsorbent techniques or other conventional methods well known in the art.

More particularly, techniques for isolating CAMP factors have been described in e.g., Skalka, B. and Smola, J. (1981) *Zbl. Bakt. Hyg., I. Abt. Orig.* A249:190–194; Skalka et al. (1980) *Zbl. Vet. Med.* B27:559–566; Skalka et al. (1979) *Zbl. Vet. Med.* B26:679–687; Bernheimer et al. (1979) *Infect. Immun.* 23:838–844; Jürgens et al. (1985) *J. Chrom.* 3:363–370; Jürgens et al. (1987) *J. Exp. Med.* 16:720–732.

Alternatively, the proteins can be recombinantly produced as described herein. As explained above, these recombinant products can take the form of partial protein sequences, full-length sequences, precursor forms that include signal sequences, mature forms without signals, or even fusion proteins (e.g., with an appropriate leader for the recombinant host, or with another subunit antigen sequence for Streptococcus or another pathogen).

The CAMP factor genes of the present invention can be isolated based on the ability of the protein products to display CAMP activity, using CAMP assays as described below. Thus, gene libraries can be constructed and the resulting clones used to transform an appropriate host cell. Colonies can be pooled and screened for clones having CAMP activity. Colonies can also be screened using polyclonal serum or monoclonal antibodies to the desired antigen.

Alternatively, once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. I, supra; *Nucleic Acid Hybridization*, supra; *Oligonucleotide Synthesis*, supra; Sambrook et al., supra. Once a clone from the screened library has been identified by positive hybridization, it can be confirmed by restriction enzyme analysis and DNA sequencing that the particular library insert contains the desired CAMP factor gene or a homolog thereof.

Alternatively, DNA sequences encoding the proteins of interest can be prepared synthetically rather than cloned. The DNA sequences can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, *DNA Cloning*: Vols. I & II, supra; Sambrook et al., supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. If signal sequences are included, they can either be the native, homologous sequences, or heterologous sequences. For example, the signal sequence for *S. uberis* CAMP factor (shown in FIG. 4A), can be used for secretion of various CAMP factors, as can a number of other signal sequences, well known in the art. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the CAMP factor of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis*, and Streptococcus spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis,*

*Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the proteins of the present invention are produced by culturing host cells transformed by an expression vector described above under conditions whereby the protein of interest is expressed. The protein is then isolated from the host cells and purified. If the expression system secretes the protein into the growth media, the protein can be purified directly from the media. If the protein is not secreted, it is isolated from cell lysates. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

The CAMP factors, fragments, analogs and chimeras containing the same, can be tested for CAMP activity using any of several standard tests. For example, CAMP factors are known to display lytic action on a variety of target cells including bovine and ovine erythrocytes. Thus, a convenient method for testing for CAMP factor activity utilizes standard hemolytic reactions using ovine or bovine erythrocytes. See, e.g., Christie et al. (1944) *Aus. J. Exp. Biol. Med. Sci.* 22:197–200; Brown et al. (1974) *Infect. Immun.* 9:377–383; Darling, C. L. (1975) *J. Clin. Microbiol.* 1:171; Wilkinsin, H. W. (1977) *J. Clin. Microbiol.* 6:42; Bernheimer et al. (1979) *Infect. Immun.* 23:838–844; Skalka, B. and Smola, J. (1981) *Zbl. Bakt. Hyg., I. Abt. Orig.* A249:190–194; Huser et al. (1983) *J. Gen. Microbiol.* 129:1295.

Activity can also be tested by monitoring the release of entrapped marker molecules from liposomes made from materials susceptible to disruption by CAMP factors. For example, CAMP activity can be monitored using [$^{14}$C] glucose-containing liposomes prepared from, e.g., sphingomyelin, cholesterol and dicetyl phosphate, and measuring the release of trapped [$^{14}$C]glucose due to disruption of the liposomes by the CAMP factor. See, e.g., Bernheimer et al. (1979) *Infect. Immun.* 23:838–844. Similarly, ATP release from liposomes in the presence of CAMP factor can be monitored as described in Sterzik et al. (1984) "Interaction of the CAMP factor from *S. agalactiae* with artificial membranes" In: Alouf et al., eds. *Bacterial protein toxins*, London: Academic Press Inc., 1984:195–196; and Sterzik et al. (1985) *Zentralbl. Bakteriol. Mikrobiol. Hyg. Abt.* 1 *Suppl.* 15:101–108. See, also Pehrenbach et al. (1984) "Interaction of amphiphilic bacterial polypeptides with artificial membranes." In: Alout et al., eds. *Bacterial protein toxins*, London: Academic Press Inc., 1984:317–324.

The CAMP factors of the present invention or their fragments can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. See, e.g., Jürgens et al. (1985) *J. Chrom.* 348:363–370. If serum containing polyclonal antibodies is used, the polyclonal antibodies can be purified by immunoaffinity chromatography, using known procedures.

Monoclonal antibodies to the CAMP factors and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444, 887; 4,452,570; 4,466,917; 4,472,500, 4,491,632; and 4,493,890. Panels of monoclonal antibodies produced against the CAMP factor of interest, or fragment thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies can also be used for passive immunization or can be combined with subunit vaccine preparations to enhance the immune response.

Vaccine Formulations and Administration

The CAMP factors of the present invention can be formulated into vaccine compositions, either alone or in combination with other antigens, for use in immunizing subjects as described below. Methods of preparing such formulations are described in, e.g., *Remington's Pharmaceutical Sciences*, Mack Publishing Company, Easton, Pa., 18 Edition, 1990. Typically, the vaccines of the present invention are prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the vaccine may also be added to the formulation. Adjuvants may include for example, muramyl dipeptides, avridine, aluminum hydroxide, dimethyldioctadecyl ammonium bromide (DDA), oils, oil-in-water emulsions, saponins, cytokines, and other substances known in the art.

The CAMP factor may be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

The CAMP factors may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the CAMP factors of the present invention include VP6 polypeptides of rotaviruses, or functional fragments thereof, as disclosed in U.S. Pat. No. 5,071,651, incorporated herein by reference. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

Furthermore, the CAMP factors (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Injectable vaccine formulations will contain a "therapeutically effective amount" of the active ingredient, that is, an amount capable of eliciting an immune response in a subject to which the composition is administered. In the treatment and prevention of mastitis, for example, a "therapeutically effective amount" would preferably be an amount which controls infection, as measured by, e.g. the ability of the composition to retain or bring the somatic cell count in milk below about 500,000 cells per ml. The exact amount is readily determined by one skilled in the art using standard tests. The CAMP factor will typically range from about 1% to about 95% (w/w) of the composition, or even higher or lower if appropriate. With the present vaccine formulations, 20 to 500 µg of active ingredient per ml of injected solution should be adequate to raise an immunological response when a dose of 1 to 3 ml per animal is administered.

To immunize a subject, the vaccine is generally administered parenterally, usually by intramuscular injection. Other modes of administration, however, such as subcutaneous, intraperitoneal and intravenous injection, are also acceptable. The quantity to be administered depends on the animal to be treated, the capacity of the animal's immune system to synthesize antibodies, and the degree of protection desired. Effective dosages can be readily established by one of ordinary skill in the art through routine trials establishing dose response curves. The subject is immunized by administration of the vaccine in at least one dose, and preferably two doses. Moreover, the animal may be administered as many doses as is required to maintain a state of immunity to infection.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The CAMP factors can also be delivered using implanted mini-pumps, well known in the art.

The CAMP factors of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK⁻ recombinant can be selected by culturing the cells in the presence of 5-bromodeoxyuridine and picking viral plaques resistant thereto.

An alternative route of administration involves gene therapy or nucleic acid immunization. Thus, nucleotide sequences (and accompanying regulatory elements) encoding the subject CAMP factors can be administered directly to a subject for in vivo translation thereof. Alternatively, gene transfer can be accomplished by transfecting the subject's calls or tissues ex vivo and reintroducing the transformed material into the host. DNA can be directly introduced into the host organism, i.e., by injection (see International Publication No. WO/90/11092; and Wolff et al. (1990) *Science* 247:1465–1468). Liposome-mediated gene transfer can also be accomplished using known methods. See, e.g., Hazinski et al. (1991) *Am. J. Respir. Cell Mol. Biol.* 4:206–209; Brigham et al. (1989) *Am. J. Med. Sci.* 298:278–281; Canonico et al. (1991) *Clin. Res.* 39:219A; and Nabel et al. (1990) *Science* 1990) 249:1285–1288. Targeting agents, such as antibodies directed against surface antigens expressed on specific cell types, can be covalently conjugated to the liposomal surface so that the nucleic acid can be delivered to specific tissues and cells susceptible to infection.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 10801 University Boulevard, Manassas, Va. 20110-2209, under the provisions of the Budapest Treaty. The accession number indicated was assigned after successful viability testing, and the requisite fees were paid. The designated deposits will be maintained for a period of thirty (30) years from the date of deposit, or for five (5) years after the last request for the deposit, whichever is longer. Should a culture become nonviable or be inadvertently destroyed, or, in the case of plasmid-containing strains, lose its plasmid, it will be replaced with a viable culture(s) of the same taxonomic description.

Should there be a discrepancy between the sequence presented in the present application and the sequence of the gene of interest in the deposited plasmid due to routine sequencing errors, the sequence in the deposited plasmid controls.

| Strain | Deposit Date | ATCC No. |
|---|---|---|
| pJLD21 in E. coli JF1754 | Jun. 9, 1995 | 69837 |

C. Experimental

Materials and Methods

Enzymes were purchased from commercial sources, and used according to the manufacturers' directions. Radionucleotides and nitrocellulose filters were also purchased from commercial sources.

In the isolation of DNA fragments, except where noted, all DNA manipulations were done according to standard procedures. See, Sambrook et al., supra. Restriction enzymes, $T_4$ DNA ligase, E. coli, DNA polymerase I, Klenow fragment, and other biological reagents can be purchased from commercial suppliers and used according to the manufacturers' directions. Double stranded DNA fragments were separated on agarose gels.

Bacterial Strains, Plasmids and Growth Conditions:

The E. coli strain used for cloning the S. uberis CAMP factor gene was JF1754 (hsdR lac gal metB leuB hisB) (McNeil, J. B. and Friesen, J. D. (1981) Mol. Gen. Genet. 184:386–393). Competent E. coli JF1754 was made as previously described (Hanahan, D. "Techniques for transformation of E. coil." In: Glover D M, ed. DNA cloning (Volume I): a practical approach. Oxford: IRL Press, 1985:109–135). E. coli cells were grown in Luria broth (Difco Laboratories) or on Luria-agar (Difco Laboratories) plates. Ampicillin was used at 50 μg/ml for the growth of E. coli strains containing recombinant plasmids. Four S. uberis strains, as well as S. agalactiae and S. aureus, were obtained from the American Type Culture Collection (ATCC Accession Nos. 9927, 13386, 13387, 19436, 27541 and 25923, respectively). Other S. uberis strains are field isolates kindly provided by M. Chirino-Trejo, University of Saskatchewan. All streptococcal strains were grown in brain heart infusion broth (BHI, Difco Laboratories) or on base #2 blood agar plates with 5% sheep blood (PML microbiologicals).

The cloning vector pTZ18R (Mead et al. (1986) Protein Eng. 1:67–74) was obtained from Pharmacia Canada Ltd.

Preparation of S. aureus Beta-toxin:

S. aureus was cultured in BHI for 18 h at 37° C. and the supernatant obtained after centrifugation at 5,000 g was sterilized by filtration through a 0.22-uM filter (Nalge company). This material, referred to as crude beta-toxin, was stored at −20° C.

CAMP Reaction

Bacteria were screened for CAMP activity as described (Schneewind et al. (1988) Infect. Immun. 56:2174–2179). Briefly, strains were streaked perpendicular to a streak of beta-toxin-producing S. aureus on blood agar plates and after 6 h–20 h incubation at 37° C., they were observed for hemolysis.

Purification of CAMP Factor

CAMP factor was partially purified from the culture supernatant of S. uberis (ATCC Accession No. 9927) by Octyl-Sepharose CL-4B (Pharmacia) chromatography as described by Jürgens et al. (1985) J. Chrom. 348:363–370.

Polyclonal Antibodies

To analyse the recombinant CAMP factor of S. uberis, polyclonal antibodies directed against the purified CAMP factor were obtained. Mice were immunized by intraperitoneal injection of 20 μg of the purified CAMP protein with complete Freund adjuvant. This primary immunization was followed 3 weeks later by the second intraperitoneal injection of the same amount of CAMP protein with incomplete Freund adjuvant and another 3 weeks later by the third intravenous injection of 20 μg of CAMP protein with incomplete Freund adjuvant. The blood serum samples were then taken 10 days later.

PAGE and Immunoblotting

Protein samples of S. agalactiae and E. coli were obtained from culture supernatants by trichloroacetic acid (TCA)-precipitation at a final concentration of 10%. SDS-polyacrylamide gel electrophoresis (PAGE) of proteins was performed as described by Laemmli (Laemmli, U. K. (1970) Nature 227:680–685). Proteins were electroblotted onto nitrocellulose membranes as recommended by the supplier (Bio-Rad) and the blots were developed as described elsewhere (Theisen, M. and Potter, A. A. (1992) J. Bacteriol. 174:17–23) with the following differences. The first antiserum used was mouse polyclonal antiserum against partially-purified S. uberis CAMP protein, and it was absorbed with antigens of the E. coli host strain as described previously (Frey et al. (1989) Infect. Immun. 57:2050–2056). The second antibody used in blotting procedure was the goat anti-mouse IgG coupled to alkaline phosphatase (Kirkegaard & Perry Laboratories, Inc.).

DNA Manipulations

All molecular techniques were as recommended by the supplier (Pharmacia Canada Ltd.) or Sambrook et al., supra. Chromosomal DNA of S. uberis was prepared from cells grown in 100 ml BHI plus 5% (w/v) glycine. Cells were pelleted and resuspended in 2.5 ml of TES buffer (30 mM Tris-HCl, 5 mM EDTA, 50 mM NaCl; pH 8.0) with 25% sucrose and 1.6 mg/ml lysozyme (Sigma). The suspension was incubated for 1 h at 37° C., followed by freezing at −70° C. The frozen cells were thawed in a 65° C. water bath. EDTA and proteinase K (Pharmacia) were added to final concentrations of 20 mM and 1.2 mg/ml, respectively, before incubation at 65° C. for 30 min. To lyse cells completely, sarkosyl was added to 1% and incubated at 37° C. for 1 h. Two ml of TE buffer (10 mM Tris-HCl, 1 mM EDTA; pH 8.9) was added prior to phenol: chloroform extraction. DNA was recovered by ethanol precipitation and was treated with RNase (Pharmacia Canada Ltd.).

Size-fractionated Sau3AI-digested chromosomal DNA fragments were isolated by sucrose density gradient centrifugation (Sambrook et al., supra).

DNA sequence was determined by the dideoxy-chain termination method of Sanger et al. (1977) Proc. Natl. Acad.

Sci. USA 74:5463–5467 on double-stranded plasmid templates by using a $T^7$ Sequencing kit (Pharmacia Canada Ltd.).

RNA Analyses

RNA from E. coli strains was isolated as described previously (Lloubes et al. (1986) Nucleic Acid Res. 14:2621–2636) with an additional RNase-free DNase I digestion. RNA from S. uberis was prepared as follows. The cell pellet from a 10 ml culture ($OD_{600}$=0.6) was resuspended in 250 µl of TE buffer (pH 8.0) containing 500 u of mutanolysin (Sigma) and incubated at 37° C. for 30 min. Lysis buffer (250 µl)(60 mM Tris-HCl pH 7.4, 200 mM NaCl, 10 mM EDTA, 2% SDS) and 100 µg/ml (final concentration) of proteinase K was added and the incubation continued for 1 h. The sample was extracted once with 65° C. phenol (water saturated, pH 4.0) and twice with room temperature phenol. RNA was recovered by ethanol precipitation and treated with DNase I (Pharmacia Canada Ltd.).

Primer extension assay was performed as described by Miller et al. (1986) Nucleic Acids Res. 14:7341–60. RNasin and moloney murine leukemia virus reverse transcriptase were obtained from Pharmacia Canada Ltd.

EXAMPLE 1

Cloning and Expression of the S. uberis CAMP Factor Gene

Chromosonal DNA of S. uberis (ATCC 9927) was partially digested with Sau3AI and size fractionated in a sucrose gradient; from this, 2- to 5-kb DNA fragments were recovered. The ends of these fragments were partially filled in with dGTP and dATP and ligated into pTZ18R which was cut with SalI and partially filled in with dTTP and dCTP. Following transformation of E. coli JF1754 competent cells, clones expressing the CAMP factor gene were identified on blood plates with ampicillin and beta-toxin on the surface. Six clones from a total of 10,000 were phenotypically hemolytic and each one mediated a distinct CAMP reaction. One of them, containing recombinant plasmid pJLD21, was selected for further study and its CAMP reaction is shown in FIGS. 1 and 2.

Figure 2:
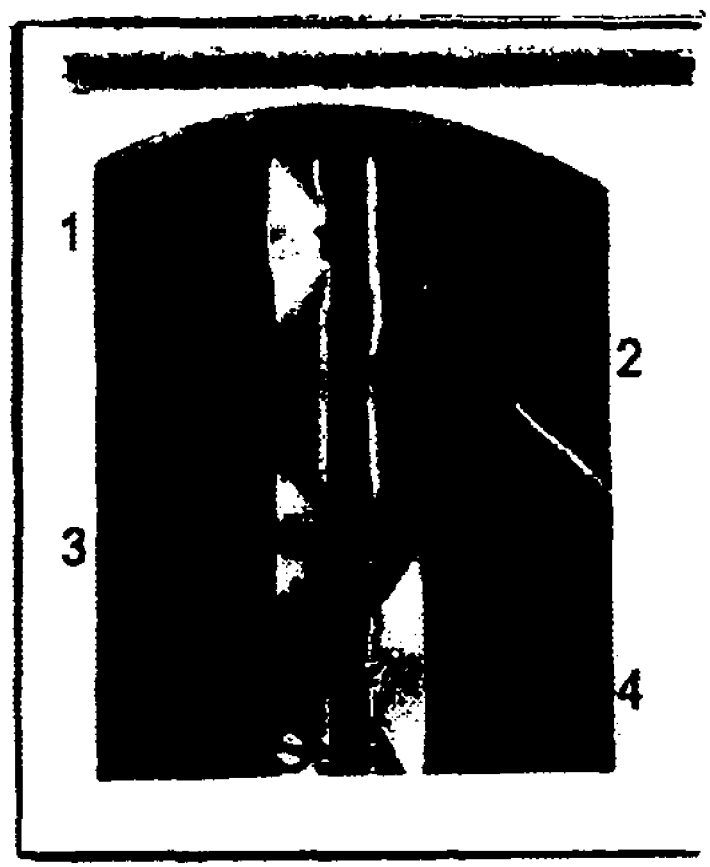
FIG. 2 shows the results of a CAMP reaction using *S. uberis* and recombinant *E. coli* clones. The CAMP reaction was done on a base #2 blood plate as described in the experimental section under Materials and Methods. Vertical streak: S, *Staphylococcus aureus*. Horizontal streak: 1, *S. uberis*; 2, *E. coli* JF1754(pTZ18R)(negative control); 3, *E. coli* JF1754(pJLD21)(CAMP-positive recombinant); 4, *E. coli* JF1754(pJLD21-2)(CAMP-positive subclone).

Plasmid pJLD21 contained a 5.2 kb insert fragment and the CAMP factor gene, cfu, was localized within a 3.2 kb BamHI fragment after the CAMP-positive subclone pJLD21-2 was generated (FIGS. 1 and 2). This subclone was further analysed with more restriction enzymes for sequencing purposes.

Figure 3A:
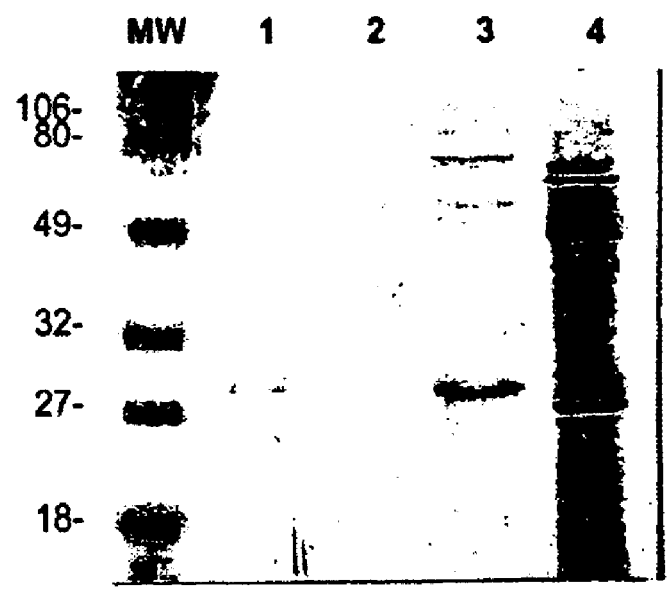
FIGS. 3A and 3B are representations of an SDS-PAGE and an immunoblot analysis, respectively, of *S. uberis* and *S. agalactiae* CAMP factors.

To study the expression of the recombinant CAMP factor, SDS-PAGE analysis of supernatant proteins from Cfu$^+$ E. coli JF1754(pJLD21) and host E. coli JF1754 (pTZ18R) was performed (FIG. 3A). Compared to the vector control, no distinguishable band was observed in the lane containing supernatant from the Cfu$^+$ clone, indicating that either expression was at a very low level or the protein was not secreted efficiently. To identify the CAMP factor encoded by pJLD21, the proteins separated by SDS-PAGE were transferred to a nitrocellulose membrane and immunoblotted (FIG. 4B). The Cfu$^+$ E. coli clone carrying pJLD21 expressed a protein with molecular weight of 28,000 (lane 2), similar to the native CAMP factor of S. uberis (lane 1).

Figure 8:
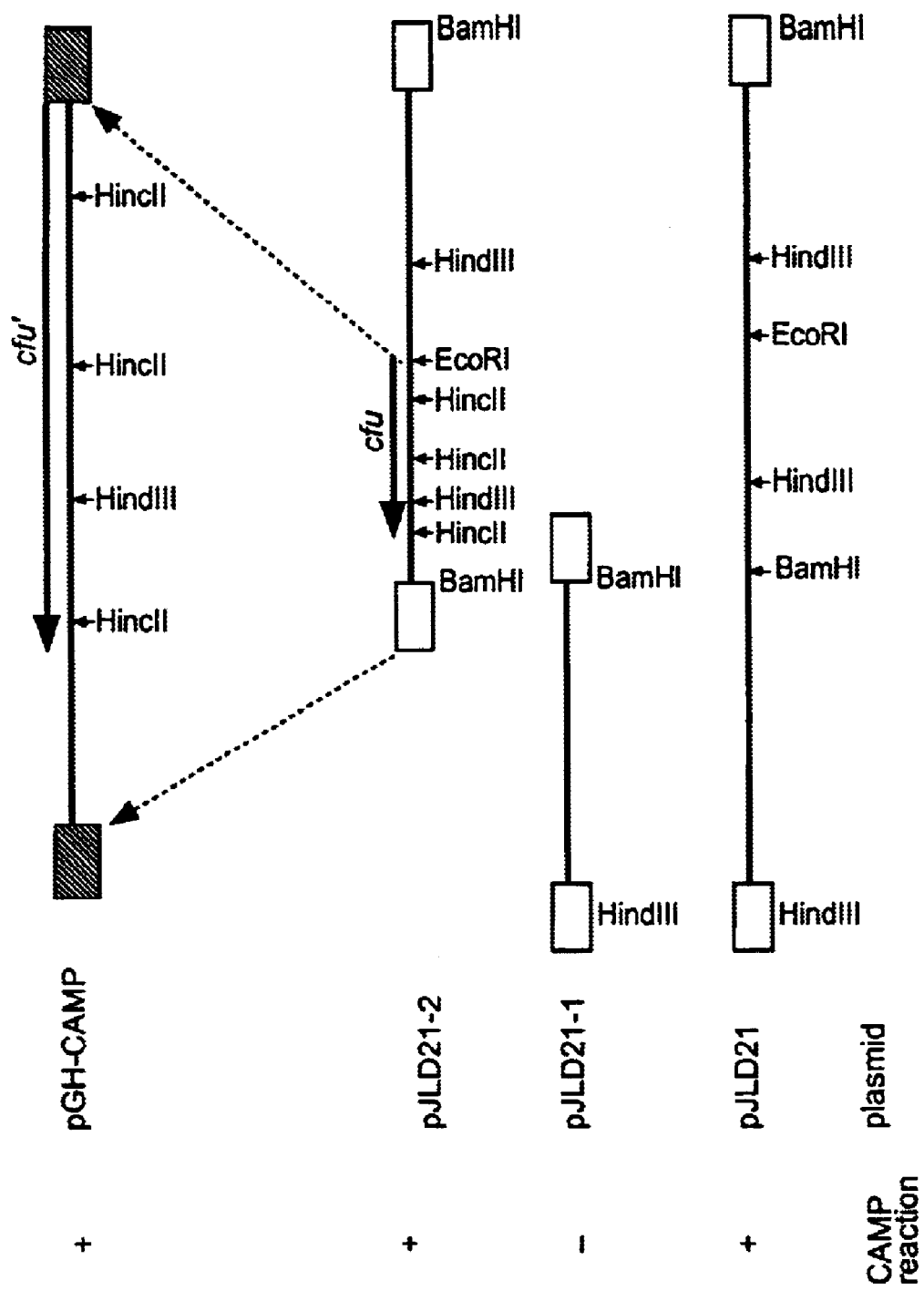
FIG. 8 depicts the construction of pGH-CAMP. The CAMP reactions for each clone from which the plasmid was derived are shown to the right of the figure; + indicates a positive reaction and − a negative reaction. Open boxes indicate pTZ18R and hatched boxes indicate pGH433.

Another expression plasmid for the S. uberis CAMP factor, pGH-CAMP, was constructed as shown in FIG. 8. In particular, A 1.7 kb EcoRI-BamHI fragment of pJLD21-2 was filled in with Klenow polymerase and inserted into pGH433 which was cut by BamHI and filled in a similar fashion. Plasmid pGH433 is an expression vector containing a tac promoter, a translational start site with restriction enzyme sites allowing ligation in all three reading frames followed by stop codons in all reading frames. See, Theisen, M. and Potter, A. A. (1992) J. Bacteriol. 174:17–23.

The expression plasmids were used to transform E. coli JF1754 (described above). The CAMP factor was prepared from inclusion bodies as described in, e.g., Rossi-Campos et al. (1992) Vaccine 10:512–518, for use in the vaccine trials below. Briefly, bacteria were grown to mid-log phase and isopropyl-β,D-thiogalactoside (IPTC) was added and the cultures were incubated with vigorous agitation at 37° C. The bacteria were harvested by centrifugation, resuspended and frozen at −70° C. The frozen cells were thawed at room temperature and lysozyme was added. A detergent mix was then added. The viscosity was reduced by sonication and protein aggregates were harvested by centrifugation. The pellets were dissolved in a minimal volume of 4 M guanidine hydrochloride. The proteins were analyzed by sodium dodecyl sulfate-polyacrylamide gel electrophoresis and the protein concentration was estimated by comparing the intensity of the coomassie blue-stained bands to a bovine serum albumin standard.

EXAMPLE 2

Nucleotide Sequence of S. uberis CAMP Factor Gene

To obtain the nucleotide sequence of the S. uberis CAMP factor gene, each of the EcoRI, HindIII, HincII and SacI fragments of pJLD21-2 was individually cloned into pTZ18R. Fragments were sequenced in both orientations as shown in FIG. 1. The complete DNA sequence is presented in FIGS. 4A–4C (SEQ ID NO:3—4). An open reading frame beginning with an ATG codon located at positions 157 to 159 and terminating with the TAA stop codon at positions 925 to 927 was found which could encode a 256-residue polypeptide with a calculated molecular weight of 28,363. The ATG start codon is preceded by the purine-rich sequence AAGAGG, which serves as a ribosome binding site in E. coli (Stormo et al. (1982) Nucleic Acids Res. 10:2971–2996).

EXAMPLE 3

Primer Extension Analysis

Figure 5:
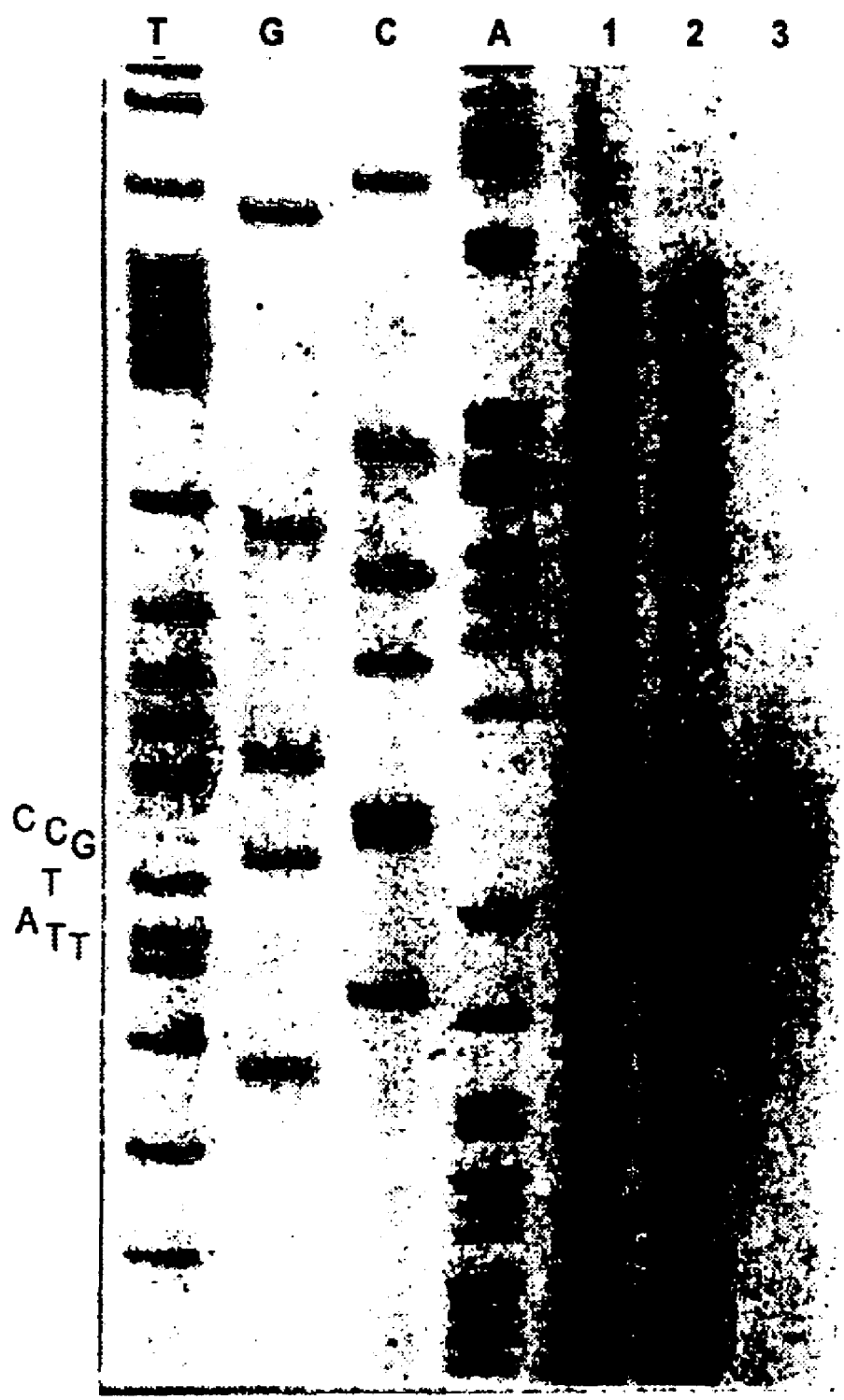
FIG. 5 shows a primer extension analysis of the promoter region of the *S. uberis* CAMP factor gene. The primer extension reactions were done as described in the examples. The cellular RNAs used were obtained from *S. uberis* (lane 1), *E. coli* JF1754(pJLD21) (lane 2), and *E. coli* JF1754 (pTZ18R) (lane 3). A dideoxy sequencing ladder was generated by using the same primer and is shown as T, G, C, A above each lane.

To localize the start site of transcription and the promoter region of the CAMP factor gene, primer extension analysis of RNA from S. uberis (ATCC 9927), E. coli JF1754 (pJLD21) and E. coli JF1754(pTZ18R) was done by using a synthetic oligonucleotide complementary to the DNA sequence from position 201 to 184. A strong primer extension product corresponding to base 91 ("T") was identified from both S. uberis and E. coli JF1754(pJLD21), but not from E. coli JF1754(pTZ18R) (FIG. 5). This data indicates that there is a major transcript of S. uberis CAMP factor gene initiated with an "A" residue (+1 in FIGS. 4A–4C; SEQ ID NO:1—2). Both −10 and −35 regions, characteristic of E. coli promoters[29], were identified at the upstream of the transcriptional start site (FIGS. 4A–4C; SEQ ID NO:1—2).

EXAMPLE 4

Comparison of the S. uberis CAMP Factor with S. agalactiae CAMP Factor

To compare the S. uberis CAMP factor with protein B of S. agalactiae, a concentrated culture supernatant of S. aga-

Figure 3B:
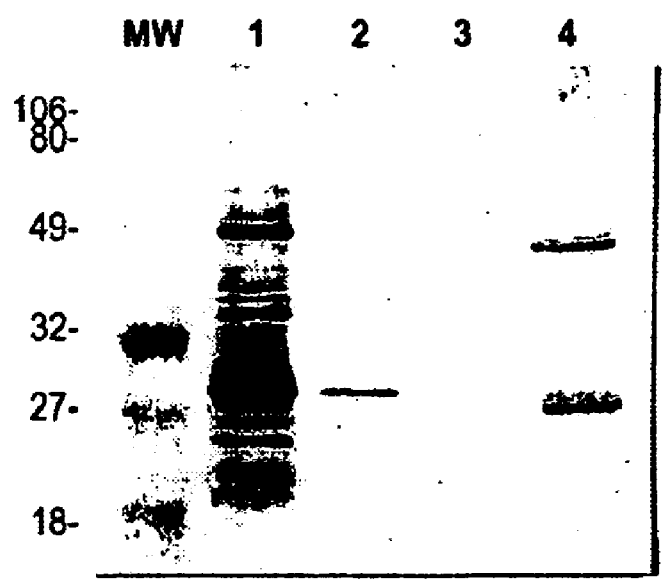

*lactiae* containing protein B (Jürgens et al. (1985) *J. Chrom.* 348:363–370) was separated by SDS-PAGE and analyzed by immunoblotting with antibodies against the purified *S. uberis* CAMP factor. A 25 kDa protein band from the *S. agalactiae* supernatant (FIG. 3A, lane 4) reacted in the immunoblot (FIG. 3B, lane 4). This data indicated that monospecific antibodies raised against the *S. uberis* CAMP factor could cross-react with *S. agalactiae* protein B. This is not surprising since alignment of the 226-amino acid sequence of the *S. agalactiae* CAMP factor with the deduced 256 amino acids of the *S. uberis* CAMP factor showed 66.4% identical residues (FIG. 6; SEQ ID NOS:3—4).

EXAMPLE 5

Distribution of CAMP Factor Genes in Eight *S. uberis* Strains

Figure 7:
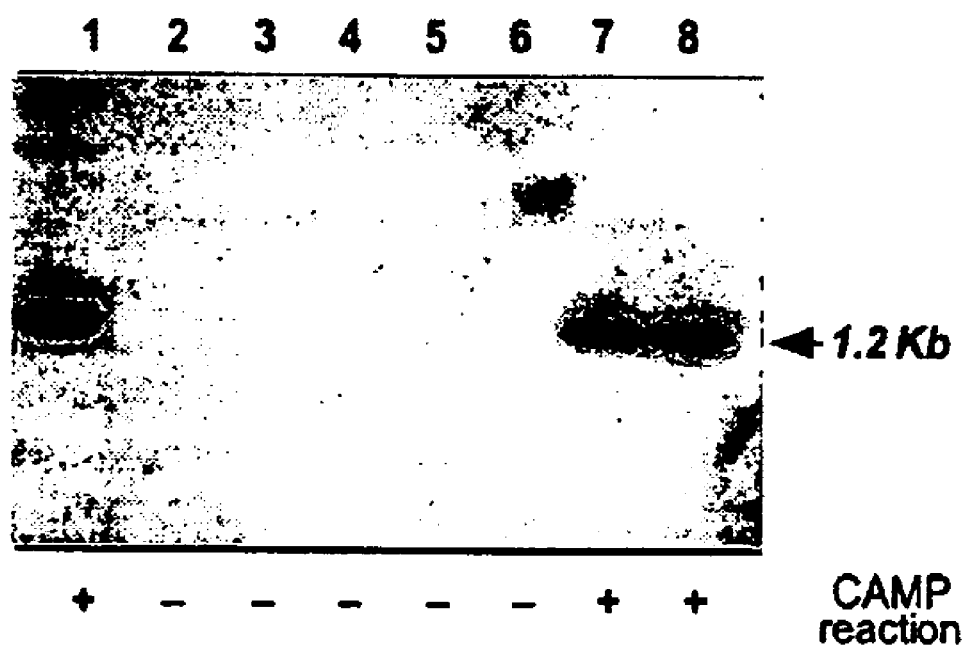
FIG. 7 shows a Southern blot analysis of different *S. uberis* strains. The origin of the probe used is indicated in FIG. 1; chromosomal DNA from each *S. uberis* strain was cut with HindIII. Lanes 1, 2, 3 and 4 are the DNA samples from ATCC strains 9927, 13386, 13387 and 19436, respectively; lanes 5, 6, 7 and 8 are the DNA samples from field isolates. The arrowhead on the right indicates the position and size of the hybridizing restriction enzyme fragments. CAMP reaction phenotype of each strain is indicated at the bottom by "+" (CAMP reaction positive) and "−" (CAMP reaction negative).

To study the distribution of the CAMP factor gene in other *S. uberis* strains, chromosomal DNA prepared from eight *S. uberis* strains was digested with the restriction endonuclease HindIII and separated on an agarose gel. Southern blot analysis with the 576 bp HindIII-EcoRI fragment of pJLD21 as a probe (FIG. 1) showed that a fragment identical in size to the HindIII fragment (1.2 kb) in pJLD21 was present in three *S. uberis* strains which were CAMP-reaction positive, while none of the CAMP reaction negative strains reacted with the probe (FIG. 7). Thus, the CAMP-negative strains do not contain the cfu gene.

EXAMPLE 6

Immunogenicity and Protective Capability of the CAMP Factor

*S. uberis* CAMP factor, encoded by pGH-CAMP, was prepared from inclusion bodies as described in Example 1. The antigen was formulated in VSA3 adjuvant which is a combination of EMULSIGEN PLUS from MVP Laboratories, Ralston, Neb. and Dimethyldioctadecyl ammonium bromide (DDA) from Kodak (Rochester N.Y.). The final concentration was 25 µg per ml of CAMP factor, 30% EMULSIGEN PLUS, 0.9% TWEEN-80, and 2.5 mg per ml of DDA. The dose volume was 2 cc containing 50 µg of recombinant antigen.

Fifteen healthy lactating dairy cows from the Pennsylvania State University Mastitis Research Herd were used to study the ability of the *S. uberis* CAMP factor to protect cows from mastitis. Animals were assigned to two groups of five cows. Treatment groups consisted of 1) experimental, given the vaccine including the *S. uberis* CAMP factor, administered intramuscularly at dry off and again 28 days later, and 2).placebo (vehicle) administered via intramuscular injection at dry off and again 28 days later.

All animals were challenged in one quarter with *S. uberis* on day four of lactation. Milk and blood samples were obtained as outlined in Table 1.

TABLE 1

| TIME | SAMPLE |
| --- | --- |
| Sampling Schedule | |
| dry off D – 0 | serum, milk, immunization |
| 14 days dry, D + 14 | serum |
| 28 days dry, D + 28 | serum, immunization |
| 52 days dry, D + 52 | serum |

TABLE 1-continued

| TIME | SAMPLE |
| --- | --- |
| Sampling Schedule | |
| calving, C – 0 | serum, milk, bacteriology |
| 4 days lactation, CH – 0 | serum, milk, bacteriology, challenge |
| 5 days lactation, CH + 1 | bacteriology |
| 6 days lactation, CH + 2 | bacteriology |
| 7 days lactation, CH + 3 | serum, milk, bacteriology |
| 14 days lactation, CH + 10 | serum, milk, bacteriology |
| 21 days lactation, CH + 17 | serum, milk, bacteriology |

The challenge strain of *S. uberis* (ATCC strain 9927) was obtained from a clinical case of bovine mastitis. The stock culture of *S. uberis* was grown in tryptic soy broth and individual aliquot were stored at –70° C. on blood beads until needed. The bacterial challenge was prepared by rolling the stock bead cultures onto esculin blood agar plates containing 5% whole blood. After 24 hours incubation at 37° C., a single colony was used to inoculate 100 ml of Ultra High Temperature pasteurized (UHT) milk and incubated for 12 hours at 37° C. The 24 hour culture was mixed well and a 100 µl aliquot was removed to inoculate a second 100 ml of UHT milk. After a second 9 hour incubation at 37° C., the culture was serially diluted in 10-fold increments using sterile saline. The colony forming units (CFU) per ml of each dilution was determined by absorbance on a spectrophotometer and confirmed by plate pouring onto blood agar plates. The dilution containing 200 CFR of *S. uberis* per ml of saline was selected for each challenge.

Total Ig titers for CAMP factor were determined by an indirect ELISA. Immunlon-2 plates were coated with antigen in carbonate buffer. Prior to use, the plates were blocked with TBST (100 mM Tris Cl, pH 8.0; 150 mM NaCl; 0.05% TWEEN-20) and 3% BSA for 1 hour. After blocking, the plates were washed with distilled water. Serum and milk samples were serially diluted in 3-fold increments using TBST containing 1% BSA. Rabbit antisera for *S. uberis* CAMP factor was also diluted and served as a positive control. Negative control samples contained TBST with 1% BSA. The diluted samples and controls were transferred to the coated plates and were incubated for 1 hour at room temperature. The plates were washed thoroughly with distilled water and all wells were incubated with a horse radish peroxidase conjugate of goat anti-IgG diluted 1:2000 in TBST containing 1% BSA. Following a 1 hour incubation at room temperature, the plates were washed with distilled water. The amount of antibody present in samples was visualized using ABT substrate. The titers of each sample were based on the absorbance reading at 405 nm with a reference wavelength of 495 nm. A positive reading for samples was one in which the absorbance was two times the absorbance of the blank (negative control). Titers were determined by taking the reciprocal of the last dilution giving a positive reading. Consistency among assay plates was monitored by the absorbance reading of positive controls.

The results are shown in TABLES 2 and 3. As can be seen, antibody titers were greater in the vaccinated animals than in the placebo group.

TABLE 2

Average Serum Titers Following
Experimental Challenge with S. uberis

| Treatment Group | Before Immunization | Before Challenge | After Challenge |
|---|---|---|---|
| Placebo A[1] | 6.75 | 45.0 | 45.0 |
| CAMP factor | 3.00 | 819.00 | 445.50 |

[1]Serum titers of samples obtained from placebo immunized animals screened for CAMP factor.

TABLE 3

Average Lacteal Antibody Titers Following
Experimental Challenge with S. uberis

| Treatment Group | Before Immunization | Before Challenge | After Challenge |
|---|---|---|---|
| Placebo A[1] | 0.00 | 0.00 | 1.33 |
| CAMP factor | 8.00 | 288.00 | 42.50 |

[1]Lacteal antibody titers of samples obtained from placebo immunized animals screened for CAMP factor.

Somatic cell counts are a traditional measure of mastitis in cows. Accordingly, milk was assayed for somatic cells using standard assay. Results are shown in TABLE 4. As is readily apparent, immunized animals had a somatic cell count within normal limits while the placebo group had cell counts indicating the presence of mastitis. Thus, the CAMP factor vaccine was effective in preventing mastitis.

TABLE 4

Average Milk Somatic Cell Counts
Following Experimental Challenge with S. uberis

| Treatment Group | Before Challenge[1] 1000 cells/ml milk | After Challenge[2] |
|---|---|---|
| Placebo A | 130.50 | 2825.25 |
| CAMP factor | 251.75 | 51.50 |

[1]Milk SCC obtained from quarters immediately prior to intramammary challenge with S. uberis
[2]Milk SCC obtained from quarters 3 days following intramammary challenge with S. uberis Thus, immunogenic CAMP factors are disclosed, as are methods of making and using the same. Although preferred embodiments of the subject invention have been described in some detail, it is understood that obvious variations can be made without departing from the spirit and the scope of the invention as defined by the appended claims.

---

What is claimed is:

1. An isolated nucleic acid molecule consisting of a sequence selected from the group consisting of: (a) a sequence encoding an immunogenic polypeptide having at least 90% sequence identity to the contiguous amino acid sequence shown at positions 1 through 256, inclusive, of SEQ ID NO:2; and (b) a sequence encoding an immunogenic polypeptide having at least 90% sequence identity to the contiguous amino acid sequence shown at positions 1–228, inclusive, of SEQ ID NO:5, wherein any sequence variation between the sequence of (a) and the sequence of amino acids shown at positions 1 through 256 of SEQ ID NO:2 is due to a conservative amino acid substitution, and any sequence variation between the sequence of (b) and the sequence of amino acids shown at positions 1–228 is due to a conservative amino acid substitution.

2. The nucleic acid molecule of claim 1 wherein said nucleic acid molecule encodes an immunogenic polypeptide having a sequence with at least 90% sequence identity to the contiguous amino acid sequence shown at positions 1 through 256, inclusive, of SEQ ID NO:2.

3. The nucleic acid molecule of claim 1 wherein said nucleic acid molecule encodes an immunogenic polypeptide having a sequence with at least 90% sequence identity to the contiguous amino acid sequence shown at positions 1–228, inclusive, of SEQ ID NO:5.

4. A recombinant vector comprising:
(a) a nucleic acid molecule encoding an immunogenic polypeptide comprising a sequence selected from the group consisting of: (i) a sequence having at least 90% sequence identity to the contiguous amino acid sequence shown at positions 1 through 256, inclusive, of SEQ ID NO:2; and (ii) a sequence having at least 90% sequence identity to the contiguous amino acid sequence shown at positions 1–228, inclusive, of SEQ ID NO:5, wherein any sequence variation between the sequence of (i) and the sequence of amino acids shown at positions 1 through 256 of SEQ ID NO:2 is due to a conservative amino acid substitution, and any sequence variation between the sequence of (ii) and the sequence of amino acids shown at positions 1–228 is due to a conservative amino acid substitution; and (b) control elements that are operably linked to said nucleic acid molecule whereby said coding sequence can be transcribed and translated in a host cell, and at least one of said control elements is heterologous to said coding sequence.

5. A recombinant vector according to claim 4, wherein said nucleic acid molecule encodes an immunogenic polypeptide which comprises a sequence having at least 90% sequence identity to the contiguous amino acid sequence shown at positions 1 through 256, inclusive, of SEQ ID NO:2.

6. A recombinant vector according to claim 4, wherein said nucleic acid molecule encodes an immunogenic polypeptide which comprises a sequence having at least 90% sequence identity to the contiguous amino acid sequence shown at positions 1–228, inclusive, of SEQ ID NO:5.

7. A host cell transformed with the recombinant vector of claim 4.

8. A host cell transformed with the recombinant vector of claim 5.

9. A host cell transformed with the recombinant vector of claim 6.

10. A method of producing a recombinant CAMP factor comprising:
(a) providing a population of host cells according to claim 7; and
(b) culturing said population of cells under conditions whereby the CAMP factor encoded by the coding sequence present in said recombinant vector is expressed.

11. A method of producing a recombinant CAMP factor comprising:
(a) providing a population of host cells according to claim 8; and
(b) culturing said population of cells under conditions whereby the CAMP factor encoded by the coding sequence present in said recombinant vector is expressed.

12. A method of producing a recombinant CAMP factor comprising:
(a) providing a population of host cells according to claim 9; and
(b) culturing said population of cells under conditions whereby the CAMP factor encoded by the coding sequence present in said recombinant vector is expressed.

13. An isolated nucleic acid molecule comprising a sequence selected from the group consisting of: (a) a sequence encoding the contiguous amino acid sequence shown at positions 1 through 256, inclusive, of SEQ ID NO:2; and (b) a sequence encoding the contiguous amino acid sequence shown at positions 1–228, inclusive, of SEQ ID NO:5.

14. The nucleic acid molecule of claim 13 wherein said sequence encodes the contiguous amino acid sequence shown at positions 1 through 256, inclusive, of SEQ ID NO:2.

15. The nucleic acid molecule of claim 13 wherein said sequence encodes the contiguous amino acid sequence shown at positions 1–228, inclusive, of SEQ ID NO:5.

16. A recombinant vector comprising:
(a) a nucleic acid molecule according to claim 13; and
(b) control elements that are operably linked to said nucleic acid molecule whereby said coding sequence can be transcribed and translated in a host cell, and at least one of said control elements is heterologous to said coding sequence.

17. A recombinant vector comprising:
(a) a nucleic acid molecule according to claim 14; and
(b) control elements that are operably linked to said nucleic acid molecule whereby said coding sequence can be transcribed and translated in a host cell, and at least one of said control elements is heterologous to said coding sequence.

18. A recombinant vector comprising:
(a) a nucleic acid molecule according to claim 15; and
(b) control elements that are operably linked to said nucleic acid molecule whereby said coding sequence can be transcribed and translated in a host cell, and at least one of said control elements is heterologous to said coding sequence.

19. A host cell transformed with the recombinant vector of claim 16.

20. A host cell transformed with the recombinant vector of claim 17.

21. A host cell transformed with the recombinant vector of claim 18.

22. A method of producing a recombinant CAMP factor comprising:
(a) providing a population of host cells according to claim 19; and
(b) culturing said population of cells under conditions whereby the CAMP factor encoded by the coding sequence present in said recombinant vector is expressed.

23. A method of producing a recombinant CAMP factor comprising:
(a) providing a population of host cells according to claim 20; and
(b) culturing said population of cells under conditions whereby the CAMP factor encoded by the coding sequence present in said recombinant vector is expressed.

24. A method of producing a recombinant CAMP factor comprising:
(a) providing a population of host cells according to claim 21; and
(b) culturing said population of cells under conditions whereby the CAMP factor encoded by the coding sequence present in said recombinant vector is expressed.

* * * * *